US008192930B2

(12) United States Patent
Vermaas et al.

(10) Patent No.: US 8,192,930 B2
(45) Date of Patent: *Jun. 5, 2012

(54) METHOD FOR SEQUENCING A POLYNUCLEOTIDE TEMPLATE

(75) Inventors: Eric Hans Vermaas, Walden (GB);
Graham John Worsley, Walden (GB);
Jonathan Mark Boutell, Waldon (GB);
Colin Lloyd Barnes, Walden (GB);
Roberto Rigatti, Walden (GB); Niall Anthony Gormley, Walden (GB);
Geoffrey Paul Smith, Walden (GB);
Vincent Peter Smith, Walden (GB);
Tobias William Barr Ost, Walden (GB);
David Bentley, Walden (GB)

(73) Assignee: Illumina Cambridge Limited, Nr Saffron Walden (GB)

( * ) Notice: Subject to any disclaimer, the term of this patent is extended or adjusted under 35 U.S.C. 154(b) by 509 days.

This patent is subject to a terminal disclaimer.

(21) Appl. No.: 12/223,759

(22) PCT Filed: Feb. 8, 2007

(86) PCT No.: PCT/GB2007/000447
§ 371 (c)(1),
(2), (4) Date: Nov. 24, 2008

(87) PCT Pub. No.: WO2007/091077
PCT Pub. Date: Aug. 16, 2007

(65) Prior Publication Data
US 2011/0009276 A1 Jan. 13, 2011

Related U.S. Application Data

(60) Provisional application No. 60/771,361, filed on Feb. 8, 2006.

(51) Int. Cl.
*C12Q 1/68* (2006.01)
(52) U.S. Cl. .............................................. 435/6.1; 506/7
(58) Field of Classification Search .................. None
See application file for complete search history.

(56) References Cited

U.S. PATENT DOCUMENTS

| 5,118,604 A | 6/1992 | Weissman et al. |
| 5,302,509 A | 4/1994 | Cheeseman |
| 5,547,839 A | 8/1996 | Dower et al. |
| 5,616,478 A | 4/1997 | Chetverin et al. |
| 5,629,158 A | 5/1997 | Uhlen |
| 5,641,658 A | 6/1997 | Adams et al. |
| 5,800,992 A | 9/1998 | Fodor et al. |

(Continued)

FOREIGN PATENT DOCUMENTS

DE 10051564 8/2002

(Continued)

OTHER PUBLICATIONS

Weimann et al. (Anal Biochem., 1996, vol. 234, p. 166-174, IDS reference).*

(Continued)

*Primary Examiner* — Stephanie K Mummert
(74) *Attorney, Agent, or Firm* — Tiffany B. Thomas

(57) ABSTRACT

The invention provides methods for pairwise sequencing of a double-stranded polynucleotide template, which methods result in the sequential determination of nucleotide sequences in two distinct and separate regions of the polynucleotide template.

26 Claims, 12 Drawing Sheets

Paired-end read POP:

Procedure
• Hybridise oligo 1 and perform sequencing run 1
• Strip extended primer with the chip on the sequencing instrument.
• Hybridise primer 2 on instrument.
• Perform sequencing run 2
• Result is two sets of sequences obtained from different positions within the same clusters.

U.S. PATENT DOCUMENTS

| | | | |
|---|---|---|---|
| 5,837,466 | A | 11/1998 | Lane et al. |
| 5,922,574 | A | 7/1999 | Minter |
| 5,935,788 | A | 8/1999 | Burmer et al. |
| 5,976,802 | A * | 11/1999 | Ansorge et al. .................. 435/6 |
| 6,060,288 | A | 5/2000 | Adams et al. |
| 6,090,592 | A | 7/2000 | Adams et al. |
| 6,107,023 | A | 8/2000 | Reyes et al. |
| 6,251,610 | B1 | 6/2001 | Gupte et al. |
| 6,322,971 | B1 | 11/2001 | Chetverin et al. |
| 6,326,489 | B1 | 12/2001 | Church et al. |
| 6,361,947 | B1 | 3/2002 | Dong et al. |
| 6,511,803 | B1 | 1/2003 | Church et al. |
| 7,115,400 | B1 | 10/2006 | Adessi et al. |
| 7,754,429 | B2 * | 7/2010 | Rigatti et al. .................. 435/6 |
| 2002/0055100 | A1 | 5/2002 | Kawashima et al. |
| 2002/0061532 | A1 | 5/2002 | Adams et al. |
| 2002/0081591 | A1 * | 6/2002 | Lukhtanov et al. ............ 435/6 |
| 2002/0098499 | A1 | 7/2002 | Asp et al. |
| 2003/0022207 | A1 | 1/2003 | Balasubramanian et al. |
| 2003/0082576 | A1 | 5/2003 | Jones et al. |
| 2003/0108867 | A1 | 6/2003 | Chee et al. |
| 2004/0002090 | A1 | 1/2004 | Mayer et al. |
| 2004/0096853 | A1 | 5/2004 | Mayer |
| 2004/0126765 | A1 | 7/2004 | Adams |
| 2005/0100900 | A1 | 5/2005 | Kawashima et al. |
| 2006/0024681 | A1 | 2/2006 | Smith et al. |
| 2006/0134633 | A1 | 6/2006 | Chen et al. |
| 2006/0292611 | A1 | 12/2006 | Berka et al. |
| 2007/0128624 | A1 | 6/2007 | Gormley et al. |
| 2008/0009420 | A1 | 1/2008 | Schroth et al. |
| 2009/0093378 | A1 | 4/2009 | Bignell et al. |

FOREIGN PATENT DOCUMENTS

| | | |
|---|---|---|
| EP | 0 201 184 | 12/1986 |
| EP | 0 224 126 | 6/1987 |
| EP | 0 356 021 | 2/1990 |
| EP | 0 374 665 | 6/1990 |
| EP | 0 438 292 | 7/1991 |
| EP | 0 534 858 | 3/1993 |
| EP | 0 665 293 | 8/1995 |
| EP | 0 763 135 | 3/1997 |
| EP | 1 256 632 | 11/2002 |
| EP | 1 591 541 | 11/2005 |
| EP | 1 647 602 | 4/2006 |
| EP | 2 032 686 | 1/2008 |
| GB | 0205153.0 | 4/2002 |
| GB | 2412170 | 9/2005 |
| GB | 0522310.2 | 12/2005 |
| WO | 89/01050 | 2/1989 |
| WO | 89/09282 | 10/1989 |
| WO | 92/10587 | 6/1992 |
| WO | 93/04199 | 3/1993 |
| WO | 94/02634 | 2/1994 |
| WO | 95/33073 | 12/1995 |
| WO | 96/04404 | 2/1996 |
| WO | 96/32504 | 10/1996 |
| WO | 98/36094 | 8/1998 |
| WO | 98/44151 | 10/1998 |
| WO | 98/44152 | 10/1998 |
| WO | 00/18957 | 4/2000 |
| WO | 00/75374 | 12/2000 |
| WO | 01/49882 | 7/2001 |
| WO | 01/79553 | 10/2001 |
| WO | 02/46456 | 6/2002 |
| WO | 03/056030 | 7/2003 |
| WO | 03/074734 | 9/2003 |
| WO | 2004/070005 | 8/2004 |
| WO | 2004/072294 | 8/2004 |
| WO | 2005/003375 | 1/2005 |
| WO | 2005/040425 | 5/2005 |
| WO | 2005/042781 | 5/2005 |
| WO | 2005/068656 | 7/2005 |
| WO | 2005/093094 | 10/2005 |
| WO | 2006/110855 | 10/2006 |
| WO | 2006/135342 | 12/2006 |
| WO | 2007/010251 | 1/2007 |
| WO | WO 2007/010252 | 1/2007 |
| WO | WO 2007/010263 | 1/2007 |
| WO | 2007/052006 | 5/2007 |
| WO | 2007/076726 | 7/2007 |
| WO | 2007/091077 | 8/2007 |
| WO | 2007/107710 | 9/2007 |
| WO | 2007/111937 | 10/2007 |
| WO | 2008/002502 | 1/2008 |

OTHER PUBLICATIONS

O'Meara et al. (Nucleic Acids Research, 2002, vol. 30, No. 17, e75, p. 1-8).*

Frommer et al. (PNAS, 1992, vol. 89, p. 1827-1831).*

Sarkar et al. (PCR Methods and Applications, 1993:2, 318-322).*

Kaderali et al. (Nucleic Acids Research, 2003, 31(6):1796-1802).*

Warren, et al., Assembling millions of short DNA sequences using SSAKE, Bioinformatics, 23:500-501 (2007).

Margulies, et al., Genome sequencing in microfabricated high-density picolitre reactors, Nature, 437:376-380 (2005).

Bennett, et al., Toward the $1000 Human Genome, Pharmacogenomics, 6:373-382 (2005).

Adessi et al., Solid phase DNA amplification: characterization of primer attachment and amplification mechanisms, Nucleic Acids Research, 28(e87):1-8 (2000).

Braslaysky et al., Sequence information can be obtained from single DNA molecules, Proc. Natl. Acad. Sci., 100:3960-3964 (2003).

Cheng et al., Chip PCR. II. Investigation of different PCR amplification systems in microfabricated silicon-glass chips, Nucleic Acids Research, 24:380-385 (1996).

Dubiley et al., Polymorphism analysis and gene detection by minisequencing on an array of gel-immobilized primers, Nucleic Acids Research, 27(e19): i-vi (1999).

Fu et al., Sequencing double-stranded DNA by strand displacement, Nucleic Acids Research, 25:677-679 (1997).

Helfman et al., Identification of clones that encode chicken tropomyosin by direct immunological screening of a cDNA expression library, Proc. Natl. Acad. Sci., 80:31-35 (1983).

Kalisch et al., Covalently linked sequencing primer linkers (splinkers) for sequence analysis of restriction fragments, Gene, 44: 263-270 (1986).

Kimmel, Preparation of cDNA and the Generation of cDNA Libraries: Overview, Methods in Enzymology, 152:307-316 (1987).

Kinzler et al., Whole genome PCR: application to the identification of sequences bound by gene regulatory proteins, Nucleic Acids Research, 17:3645-3653 (1989).

Lucito et al., Genetic analysis using genomic representations, Proc. Natl. Acad. Sci., 95:4487-4492 (1998).

Matsunaga et al., Selecting and amplifying one fragment from a DNA fragment mixture by polymerase chain reaction with a pair of selective primers, Electrophoresis, 17:1833-1840 (1996).

Ng, et al., Multiplex sequencing of paired-end ditags (MS-PET): A Strategy for the Ultra-High-Throughput Analysis of Transcriptomes and Genomes, Nucleic Acids Research, 34(e84): 1-10 (2006).

Oroskar et al., Detection of immobilized amplicons by ELISA-like techniques, Clinical Chemistry, 42:1547-1555 (1996).

Roach et al., Pairwise End Sequencing: A Unified Approach to Genomic Mapping and Sequencing, Genomics, 26:345-353 (1995).

Saiki et al., Analysis of enzymatically amplified β-globin and HLA-DQα DNA with allele-specific oligonucleotide probes, Nature, 324:163-166 (1986).

Saiki et al., Primer-Directed Enzymatic Amplification of DNA with a Thermostable DNA with a Thermostable DNA Polymerase, Science, 239:487-491 (1988).

San Luis et al., Analysis of a gene (vch) encoding hemolysin isolated and sequenced from Vibrio campbeffii, J. Gen. Appl. Microbiol., 52:303-313 (2006).

Sanger et al., Cloning in Single-stranded Bacteriophage as an Aid to Rapid DNA Sequencing, J. Mol. Biol., 143:161-178 (1980).

Shapero et al., SNP Genotyping by Multiplexed Solid-Phase Amplification and Fluorescent Minisequencing, Genome Research, 11:1926-1934 (2001).

Shendure, et al., Accurate Multiplex Polony Sequencing of an Evolved Bacterial Genome, Science, 309:1728-1732 (2005).

Shi, Enabling Large-Scale Pharmacogenetic Studies by High-Throughput Mutation Detection and Genotyping Technologies, Clinical Chemistry, 47:164-172 (2001).

Solexa, Solexa Application Note: DNA Sequencing, (2006).

Sterky et al., Direct sequencing of bacterial artificial chromosomes (BACs) and prokaryotic genomes by biotin-capture PCR, Journal of Biotechnology, 60:119-129 (1998).

Strick et al., Stress-Induced Structural Transitions in DNA and Proteins, Annu. Rev. Biophys. Struct., 29:523-543 (2000).

Velculescu et al., Serial Analysis of Gene Expression, Science, 270:484-487 (1995).

Westin et al., Anchored multiplex amplification on a microelectronic chip array, Nature Biotechnology, 18:199-204 (2000).

Wiemann et al., "Doublex" Fluorescent DNA Sequencing: Two Independent Sequences Obtained Simultaneously in One Reaction with Internal Labeling and Unlabeled Primers, Analytical Biochemistry, 234:166-174 (1996).

\* cited by examiner

One of the Five Monotemplate Sequences

```
                    -------p7-------                                          Region of variable 2nd read insert – position of 2nd read
  1 TTCCTTCTGC AGCAAGCAGA AGACGGCATA CGAGCCATTCC TGCTGAACCG AACAGGCGGG GAGCGTGATC GGAAGAGCGT CGTGTAGGGA AAGAGTGTGA
    AAGGAAGACG TCGTTCGTCT TCTGCCGTAT GCTCGTAAGG ACGACTTGGC TTGTCCGCCC CTCGCACTAG CCTTCTCGCA GCACATCCCT TTCTCACACT
                                                            Direction of sequencing read 2
                                                            ←

101 GATCTTTTAT CATCTCCATA AAACAAAACC CGCCGTAGCG AGTTCAGATA AAATAAATCC CCGCGAGTGC GAGGATTGTT ATGTAATATT GGGTTTAATC
    CTAGAAAATA GTAGAGGTAT TTTGTTTTGG GCGGCATCGC TCAAGTCTAT TTTATTTAGG GGCGCTCACG CTCCTAACAA TACATTATAA CCCAAATTAG

201 ATCTATATGT TTTGTACAGA GAGGGCAAGT ATCGTTTCCA CCGTACTCGT GATAATAATT TTGCACGGTA TCAGTCATTT CTCGCACATT GCAGAATGGG
    TAGATATACA AAACATGTCT CTCCCGTTCA TAGCAAAGGT GGCATGAGCA CTATTATTAA AACGTGCCAT AGTCAGTAAA GAGCGTGTAA CGTCTTACCC

-------p5-------
301 GATTTGTCTT CATTAGACTT ATAAACCTTC ATGGAATATT TGTATGCCGA CTCTATATCT ATACCTTCAT CTCGGTGGTC GCCGTATCAT TCTGCAGACG T
    CTAAACAGAA GTAATCTGAA TATTTGGAAG TACCTTATAA ACATACGGCT GAGATATAGA TATGGAAGTA TATGGAAGTA CGGCCACCAG CGGCATAGTA AGACGTCTGC A
                                       →
                                       Direction of sequencing read 1
                                       Position of 1st read
```

Seq primer for first read: 5' AATGATACGGCGACCACCGAGATGAAGGTATAGAT
Seq primer for second read: 5' ACACTCTTTCCCTACACGACGCTCTTCCGATC

Fig. 12

METHOD FOR SEQUENCING A POLYNUCLEOTIDE TEMPLATE

CROSS REFERENCE TO RELATED APPLICATIONS

The present application is a National Stage Application claiming the priority of co-pending PCT Application No. PCT/GB2007/000447, filed Feb. 8, 2007, which in turn, claims priority from U.S. patent application Ser. No. 60/771,361, filed Feb. 8, 2006. Applicants claim the benefits of 35 U.S.C. §120 as to the PCT application and priority under 35 U.S.C. §119 as to the said United States application, and the entire disclosures of both applications are incorporated herein by reference in their entireties.

FIELD OF THE INVENTION

The invention relates to methods for pairwise sequencing of a double-stranded polynucleotide template, which methods result in the sequential determination of nucleotide sequences in two distinct and separate regions of the polynucleotide template.

BACKGROUND TO THE INVENTION

Advances in the study of biological molecules have been led, in part, by improvement in technologies used to characterise the molecules or their biological reactions. In particular, the study of the nucleic acids DNA and RNA has benefited from developing technologies used for sequence analysis.

U.S. Pat. No. 5,302,509 describes a method for sequencing a polynucleotide template which involves performing multiple extension reactions using a DNA polymerase or DNA ligase to successively incorporate labelled nucleotides or polynucleotides complementary to a template strand. In such a "sequencing by synthesis" reaction a new nucleotide strand base-paired to the template strand is built up in the 5' to 3' direction by successive incorporation of individual nucleotides complementary to the template strand. The substrate nucleoside triphosphates used in the sequencing reaction are blocked to prevent over-incorporation and labelled differently, permitting determination of the identity of the incorporated nucleotide as successive nucleotides are added.

In order to carry out accurate sequencing a reversible chain-terminating structural modification or "blocking group" may be added to the substrate nucleotides to ensure that nucleotides are incorporated one at a time in a controlled manner. As each single nucleotide is incorporated, the blocking group prevents any further nucleotide incorporation into the polynucleotide chain. Once the identity of the last-incorporated labelled nucleotide has been determined the label moiety and blocking group are removed, allowing the next blocked, labelled nucleotide to be incorporated in a subsequent round of sequencing.

In certain circumstances the amount of sequence data that can be reliably obtained with the use of sequencing-by-synthesis techniques, particularly when using blocked, labelled nucleotides, may be limited. In some circumstances the sequencing "run" may be limited to a number of bases that permits sequence realignment with the human genome, typically around 25-30 cycles of incorporation. Whilst sequencing runs of this length are extremely useful, particularly in applications such as, for example, SNP analysis and genotyping, it would be advantageous in many circumstances to be able to reliably obtain further sequence data for the same template molecule.

The technique of "paired-end" or "pairwise" sequencing is generally known in the art of molecular biology, particularly in the context of whole-genomic shotgun sequencing (Siegel A. F. et al., Genomics. 2000, 68: 237-246; Roach J. C. et al., Genomics. 1995, 26: 345-353). Paired-end sequencing allows the determination of two "reads" of sequence from two places on a single polynucleotide duplex. The advantage of the paired-end approach is that there is significantly more information to be gained from sequencing two stretches each of "n" bases from a single template than from sequencing "n" bases from each of two independent templates in a random fashion. With the use of appropriate software tools for the assembly of sequence information (Millikin S. C. et al., Genome Res. 2003, 13: 81-90; Kent, W. J. et al., Genome Res. 2001, 11: 1541-8) it is possible to make use of the knowledge that the "paired-end" sequences are not completely random, but are known to occur on a single duplex, and are therefore linked or paired in the genome. This information has been shown to greatly aid the assembly of whole genome sequences into a consensus sequence.

Paired-end sequencing has typically been performed by making use of specialized circular shotgun cloning vectors known in the art. After cutting the vector at a specific single site, the template DNA to be sequenced (typically genomic DNA) is inserted into the vector and the ends resealed to form a new construct. The vector sequences flanking the insert DNA include binding sites for sequencing primers which permit sequencing of the insert DNA on opposite strands.

A disadvantage of this approach is that it requires time-consuming cloning of the DNA templates it is desired to sequence into an appropriate sequencing vector. Furthermore, because of the need to clone the DNA template into a vector in order to position binding sites for sequencing primers at both ends of the template fragment it is extremely difficult to make use of array-based sequencing techniques. With array-based techniques it is generally only possible to sequence from one end of a nucleotide template, this often being the end proximal to the point of attachment to the array.

WO 2004/070005 describes a method for double-ended sequencing of a polynucleotide template which can be carried out on a solid support. The method relies on simultaneous hybridisation of two or more primers to a target polynucleotide in a single primer hybridization step. Following the hybridization step, all of the primers hybridized to the template are blocked except for one, which has a free 3' hydroxyl group which serves as an initiation point for a first sequencing reaction. Sequencing proceeds until no further chain elongation is possible, or else the sequencing reaction is terminated. Then one of the blocked primers is unblocked to give a free 3' hydroxyl and a second sequencing reaction is performed from this initiation point. Thus, the template remains intact and attached to the solid support throughout.

A major drawback of this approach based on hybridisation of blocked and unblocked primers is that if it is desired to sequence two regions on complementary strands of a double-stranded nucleic acid template then it is necessary to hybridise primers to both complementary strands of the template in a single hybridisation step. Since both strands of the template remain intact and attached to the solid support, hybridisation of the primers to cognate sequences in the template strands will generally be unfavourable, against formation of a duplex by annealing of the two complementary strands of the template. A further drawback is the need to ensure the chemical blocking of the first primer to allow sequencing of the second primer. The nature of the non immobilised beads described in the application means that removal of the primers from the beads is not straightforward, and thus the sequencing runs are less than optimal unless the first primer is completely blocked.

WO 98/44151 and WO 00/18957 both describe methods of nucleic acid amplification which allow amplification products to be immobilised on a solid support in order to form arrays comprised of clusters or "colonies" formed from a plurality of identical immobilised polynucleotide strands and a plurality of identical immobilised complementary strands. The nucleic acid molecules present in DNA colonies on the clustered arrays prepared according to these methods can provide templates for sequencing reactions, for example as described in WO 98/44152 but to date only a single sequencing read can be obtained from one type of immobilised strand in each colony.

SUMMARY OF THE INVENTION

The present inventors have developed a method for paired-end, or pairwise, sequencing of double-stranded polynucleotide templates, including double-stranded templates present on clustered arrays, such as those described herein. The term pairwise sequencing refers to a pair of reads obtained by sequencing two distinct regions, either on the same strand or the complementary strand of a target polynucleotide duplex. Using the method of the invention it is possible to obtain two linked or paired reads of sequence information from each double-stranded template on a clustered array, rather than just a single sequencing read as can be obtained with prior art methods.

According to the invention there is provided a method for pairwise sequencing of first and second regions of a target double-stranded polynucleotide, wherein said first and second regions are in the same target double-stranded polynucleotide, the method comprising:
(a) providing a solid support having immobilised thereon a plurality of double stranded template polynucleotides each formed from complementary first and second template strands linked to the solid support at their 5' ends;
(b) treating the plurality of double stranded template polynucleotides to denature said double stranded template polynucleotides to facilitate hybridisation of a sequencing primer;
(c) hybridising a first sequencing primer to one of the template strands generated in part (b);
(d) performing a first sequencing reaction by sequential addition of nucleotides to the first sequencing primer to generate a first extended sequencing primer and determine the sequence of a first region of the target polynucleotide in the first template strand;
(e) removing the first extended sequencing primer from step (d);
(f) hybridising a second sequencing primer to one of the template strands; and
(g) performing a second sequencing reaction by sequential addition of nucleotides to the second sequencing primer to generate a second extended sequencing primer and determine the sequence of a second region of the target polynucleotide, wherein determining the sequences of the first and second regions of the target polynucleotide achieves pairwise sequencing of said first and second regions of said target double-stranded polynucleotide.

In one embodiment, both strands of the original polynucleotide duplex remain immobilised, and two primers with different sequences are used to generate each of the sequencing runs. Steps (b) and (e) may involve a thermal or chemical treatment such as 0.1 M sodium hydroxide to denature the surface bound double stranded polynucleotides.

In another embodiment, the target double stranded polynucleotide may also be prepared such that it contains a region of known sequence internal to two regions of unknown sequence. The known sequence may contain a recognition site for cleavage with a restriction endonuclease. Cleavage with a restriction enzyme would result in two separate polynucleotides, each immobilised through the 5'-end. The two polynucleotides may then be subject to denaturing conditions, resulting in two single stranded polynucleotides immobilised through the 5'-end. Each single stranded polynucleotide can be sequenced sequentially to give two separate reads from the one original target In another embodiment, the target double stranded polynucleotide may again be prepared such that it contains a region of known sequence internal to two regions of unknown sequence. One end of the immobilised polynucleotide may be cleaved from the surface, and the resulting polynucleotide denatured. The resultant single stranded polynucleotide, anchored via the 5'-end contains two distinct regions able to hybridise a sequencing primer; and two reads may be obtained in sequence.

BRIEF DESCRIPTION OF THE FIGURES

FIG. 12 shows the structure and sequence of an exemplary double stranded DNA template used for solid phase amplification in the accompanying examples. Sequences of the amplification primers P5 and P7 are shown in bold type.

DETAILED DESCRIPTION OF THE INVENTION

Figure 1:
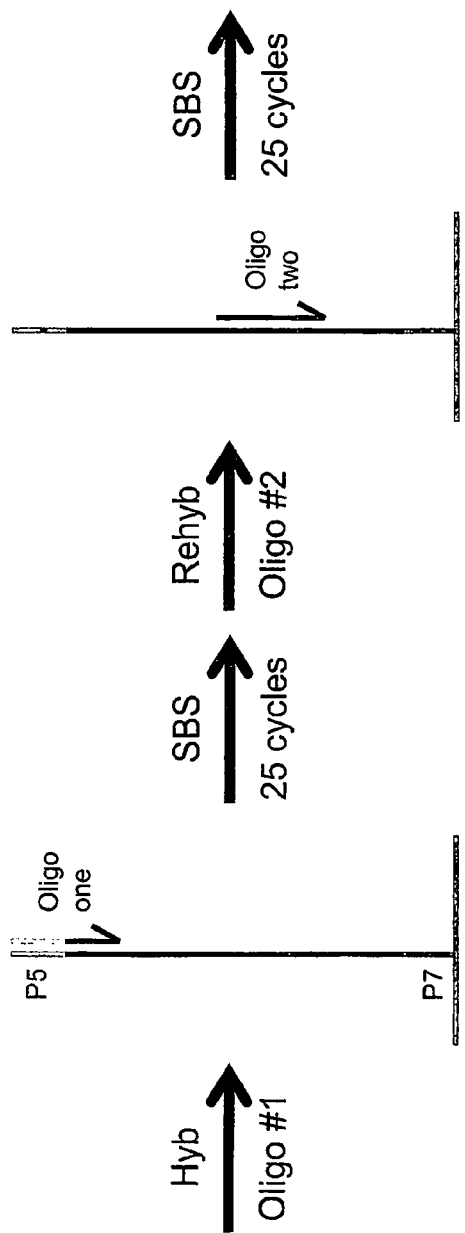
FIG. 1 shows a schematic illustration of a paired-end read. In this procedure a first oligonucleotide (oligo 1) is hybridised to a template to be sequenced and used to prime a first sequencing run (run 1, single base sequencing SBS through 25 cycles). Oligo 1 is then stripped from the template and a second primer (oligo 2) hybridised to a different region of the same template and used to prime a second sequencing run (run 2, single base sequencing SBS through 25 cycles). The result is two sequencing reads obtained from different positions within the same template.

The invention provides methods for sequencing two regions of a target double-stranded polynucleotide template, referred to herein as the first and second regions for sequence determination. The first and second regions for sequence determination are either on the same strand, or on complementary strands, of the double-stranded polynucleotide template, which are referred to herein respectively as first and second template strands.

The starting point for the method of the invention is the provision of a plurality of template polynucleotide duplexes immobilised on a solid support in the form of amplified clusters as described in WO9844151 and WO00018957, whose contents are incorporated herein by reference. Each of the duplexes within a particular cluster comprises the same double-stranded target region to be sequenced. The duplexes are each formed from complementary first and second template strands which are linked to the solid support at or near to their 5' ends. Typically, the template polynucleotide duplexes will be provided in the form of a clustered array.

WO07010252 also describes a method of reading both the first and second template strands from each cluster, but suffers from the disadvantage that only half the strands in each cluster are sequenced. This diminishes the signal intensity of the sequencing reads. The methodology described herein allows the sequencing of essentially all of the copies of each strand in each cluster, and therefore produces a signal of greater intensity than the previous methodology. This property of the present methodology confers greater sensitivity with respect to signal detection and means that longer reads can be obtained from smaller clusters than the prior art.

When referring to immobilisation or attachment of molecules (e.g. nucleic acids) to a solid support, the terms "immobilised" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to the support under the conditions in which it is intended to use the support, for example in applications requiring nucleic acid amplification and/or sequencing.

Certain embodiments of the invention may make use of solid supports comprised of an inert substrate or matrix (e.g. glass slides, polymer beads etc) which is been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

As will be apparent to the skilled reader, references herein to a particular nucleic acid sequence may, depending on the context, also refer to nucleic acid molecules which comprise the nucleic acid sequence. Sequencing of a target fragment means that a read of the chronological order of bases is established. The bases do not, however, need to be contiguous, nor does every base on the entire fragment have to be sequenced.

The following passages describe different aspects of the invention in greater detail. Each aspect of the invention may be combined with any other aspect or aspects of the invention unless clearly indicated to the contrary. In particular, any feature indicated as being particular, preferred or advantageous may be combined with any other feature or features indicated as being particular, preferred or advantageous.

The terms 'target nucleic acid sequence', 'target nucleic acid molecule', 'target nucleic acid' and 'target nucleic acid fragment' may be used interchangeably to refer to nucleic acid molecules that it is desired to sequence on an array according to the invention. The target nucleic acid may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample that has been randomly fragmented. The targets can be processed into templates suitable for amplification by the placement of universal amplification sequences at the ends of each target fragment. The targets can also be obtained from a primary RNA sample by reverse transcription into cDNA.

As used herein, the term 'polynucleotide' refers to deoxyribonucleic acid (DNA), but where appropriate the skilled artisan will recognise that the method may also be applied to ribonucleic acid (RNA). The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase.

The primary polynucleotide molecules may originate in double-stranded DNA (dsDNA) form (e.g. genomic DNA fragments, PCR and amplification products and the like) or may have originated in single-stranded form, as DNA or RNA, and been converted to dsDNA form. By way of example, mRNA molecules may be copied into double-stranded cDNAs suitable for use in the method of the invention using standard techniques well known in the art. The precise sequence of the primary polynucleotide molecules is generally not material to the invention, and may be known or unknown.

In a particular embodiment, the primary polynucleotide molecules are DNA molecules. More particularly, the primary polynucleotide molecules represent the entire genetic complement of an organism, and are genomic DNA molecules which include both intron and exon sequences (coding sequence), as well as non-coding regulatory sequences such as promoter and enhancer sequences. In an embodiment wherein genomic DNA molecules are used, genome-wide analysis or analysis of the entire genome may be achieved. It is, however, envisaged that particular sub-sets of polynucleotide sequences or genomic DNA could also be used, such as, for example, particular chromosomes. Yet more particularly, the sequence of the primary polynucleotide molecules is not known. Still yet more particularly, the primary polynucleotide molecules are human genomic DNA molecules. The DNA target molecules may be treated chemically or enzymatically, either prior to, or subsequent to any random fragmentation processes, and prior to or subsequent to the ligation of the adaptor sequences.

Random fragmentation refers to the fragmentation of a polynucleotide molecule in a non-ordered fashion by enzymatic, chemical or mechanical means. Such fragmentation methods are known in the art and utilise standard methods (Sambrook and Russell, Molecular Cloning, A Laboratory Manual, third edition). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). Moreover, random fragmentation is designed to produce fragments irrespective of the sequence identity or position of nucleotides comprising and/or surrounding the break. More particularly, random fragmentation is achieved by mechanical means such as nebulisation or sonication and produces fragments of about 50 base pairs in length to about 1500 base pairs in length, still more particularly 50-700 base pairs in length, yet more particularly 50-400 base pairs in length. Most particularly, the method is used to generate smaller fragments of from 50-150 base pairs in length.

Fragmentation of polynucleotide molecules by mechanical means (nebulization, sonication and Hydroshear for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

In a particular embodiment, the target polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example, deoxyadenosine (A) to the 3' ends of, for example, PCR products. Such enzymes can be utilised to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, whilst the adaptor polynucleotide construct could be a T-construct with a compatible 'T' overhang present on the 3' terminus of each duplex region of the adaptor construct. This end modification also prevents self-ligation of both vector and target such that there is a bias towards formation of the combined ligated adaptor-target sequences.

Paired reads can be obtained on fragments of any length, for example PCR amplicons of 2-10 Kb or DNA clones isolated from bacteria or other biological sources. The targets may be the ends of phosmid molecules of around 40 kB or the ends of Bacterial artifical chromosomes (BAC's) of around 100-200 kB. The ends of targets derived from such sources may be sequenced without fragmentation to obtain the reads from the ends of each unfragmented target, or the target may be fragmented. The fragmented targets may be size selected, for example by gel electrophoresis, to obtain a narrow size distribution on the target fragments. Paired reads spaced throughout the sample may be used as a tool for de-novo assembly of a previously unsequenced sample, as well as for resequencing a sample where a reference genome is available. The methods described herein are suitable for use with nucleic acid molecules obtained from any source, where knowledge of the sequences at either end of the molecules is desired.

In order to sequence two regions of a given target double-stranded polynucleotide using the method of the invention, it is necessary to carry out sequential sequencing reactions. To enable two separate sequencing reactions it is in turn necessary to sequentially hybridise to two different single-stranded regions to serve as templates for sequencing. Formation of suitable single-stranded regions for sequencing can be achieved by any of the ways described herein.

Sequential Hybridisation

The immobilised duplex contains two complementary strands, each immobilised through the 5'-end to the surface. Denaturing the double stranded polynucleotide results in two single stranded polynucleotides; each capable of hybridising a different sequencing primer. Using a first sequencing primer complementary to the 3'-end of one of the bound strands, allows a sequencing read to be obtained from one of the strands. This sequencing run can then be denatured; and a second primer complementary to the 3'-end of the other strand can be hybridised. The sequencing protocol can then be repeated to obtain a second run; at the opposite end of the polynucleotide molecule of the first run.

The denaturing treatment used to denature the immobilised polynucleotide, or remove the first sequencing primer can be heat to a temperature in excess of 95° C., or a chemical treatment with a denaturing solution such as 0.1 M sodium hydroxide; 50% formamide or 8 M urea solution.

The sequencing primers can remain immobilised during the first and second reads. If the double stranded polynucleotide is designed to contain a sequence selective nicking site on each strand, the sequencing reads can be performed sequentially, using the 3' side of the nicked strand as an initiation point, after each strand is nicked. The 5-end of the nicked strand remains immobilised, and can be blocked after the first sequencing run, before treatment to nick the second strand is performed. In this case the duplex is not denatured to allow hybridisation of a sequencing primer, but the first strand is nicked to allow a part of the original duplex to function as a sequencing primer and sequence the second strand. The second read is commenced by a nick of the second strand of the duplex, allowing the read of the first strand. In this embodiment, it is important not to subject the array to denaturing conditions at any point, since during the second read, the template is only attached to the surface by hybridisation.

Cluster Cleavage Using a Restriction Endonuclease

Figure 8:
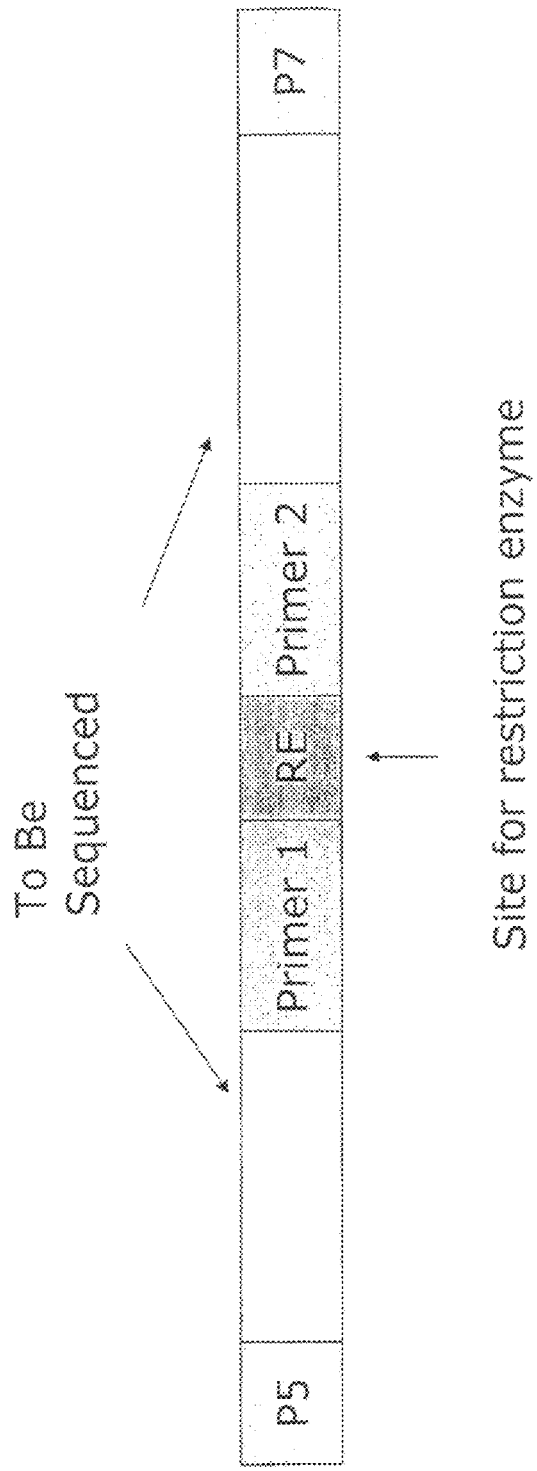
FIG. 8 shows a schematic of the method of the invention wherein the central known region comprises a site for a particular restriction enzyme. Upon treatment with the restriction enzyme, two sequencing reads can be obtained from the central region of the amplified fragments. More specifically, one read can be obtained from each strand of the immobilised duplex.

The double stranded polynucleotide templates comprise sequences of unknown target DNA between known adaptors at the ends of the sequences. However, it is straightforward to use molecular biology techniques to construct a polynucleotide where there is also a known region of nucleotide sequence splitting the unknown region in two. The template polynucleotide can thus be represented as having a known end, a stretch of unknown sequence, a known adaptor region, another unknown sequence, and a known second end, herein defined as adaptor-target-adaptor-target-adaptor constructs if they are not further amplified, or primer-target-adaptor-target-primer if the initial adaptor-target-adaptor-target-adaptors are subject to amplification. The internal sequences can be designed to contain two sequencing primer sites; as well as a site that allows sequence selective cutting of both strands of the duplex, for example a restriction endonuclease recognition site, as shown in FIG. 8. Such restriction endonuclease cuts give two anchored polynucleotide duplexes immobilised at the 5' end of one of the strands. The immobilised duplexes can be denatured by heating or chemical treatment, resulting in two non-complementary single stranded polynucleotides immobilised in close proximity. Each of these non complementary strands can be sequenced using different sequencing primers to give two reads derived from the original polynucleotide duplex.

Construction of the double stranded polynucleotide templates with an internal primer region can be performed by ligating the randomised genomic fragments into a linearised vector to re-make the circular construct. Cutting away from the known sections of the circularised vector into the unknown region using remote cutting restriction enzymes such as MmeI or EcoP15, allows the central region of the unknown sequences to be removed. EcoP15I is a type III restriction enzyme that recognizes the sequence motif CAGCAG and cleaves the double stranded DNA molecule 27 base pairs downstream of the CAGCAG motif. The cut site contains a 2 base 5'-overhang that can be end repaired to give a 27 base blunt ended duplex. Under normal in vivo conditions EcoP15I requires two CAGCAG motifs oriented in a head to head orientation on opposite strands of the double stranded molecule, and then the enzyme cleaves the duplex at only one of the two sites. However, under specific in vitro conditions in the presence of the antibiotic compound sinefungin (Sigma cat number S8559) EcoP15I has the desired effect of inducing cleavage of a double stranded duplex at all CAGCAG sequences present in a sequence irrespective of number or orientation, as shown by Raghavendra & Rao (Biochem Biophys Res Commun. 2005 Sep. 2; 334 (3):803-11), which is incorporated herein in its entirety, however to the best of our knowledge, the use of sinefungin, or an analogue thereof in the preparation of ditag libraries using EcoP15 or other type III restriction endonucleases is previously unreported.

Figure 4:
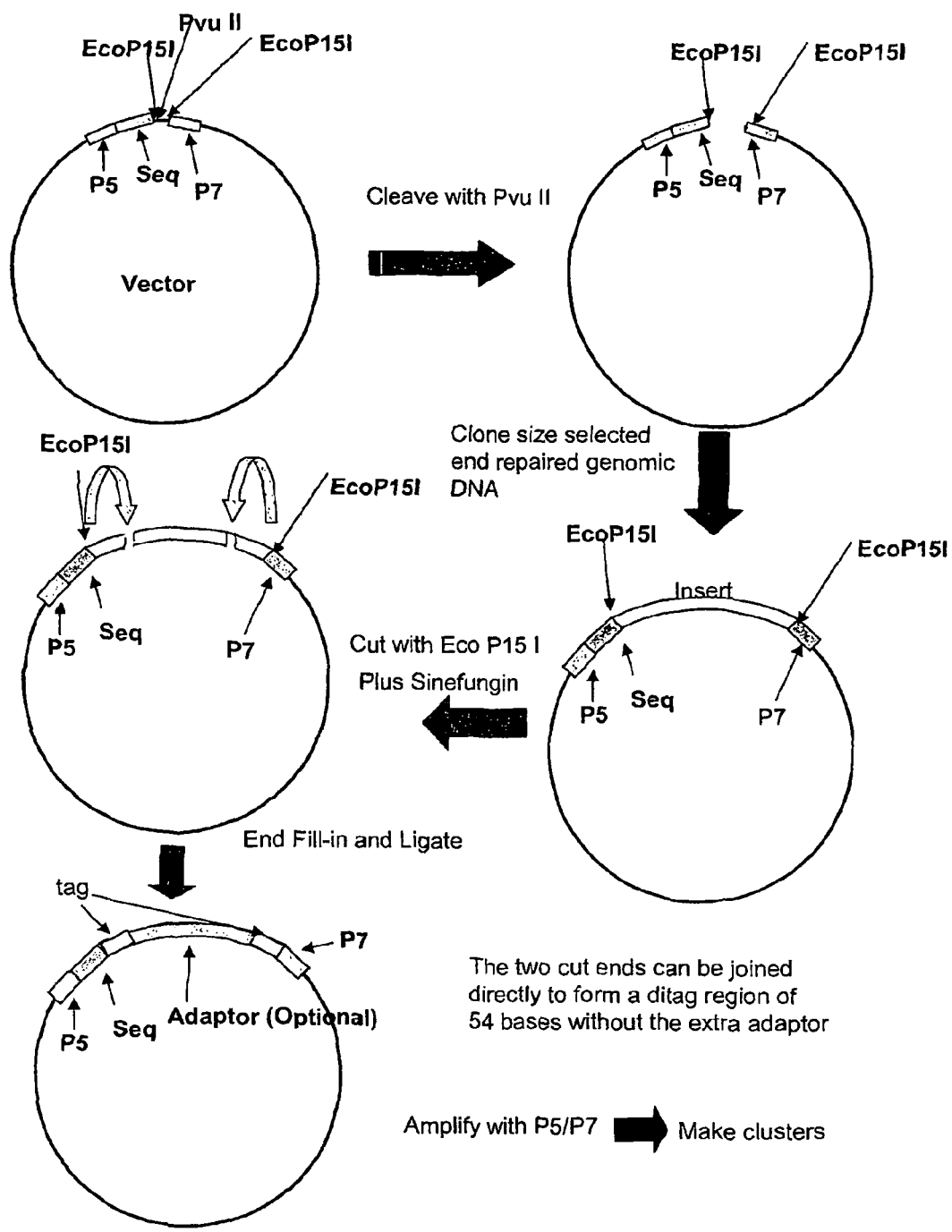
FIG. 4 shows a schematic of methods for constructing polynucleotide molecules with known sequence between unknown sequences, wherein restriction enzymes are used to make ditag sequences (vector-target-target-vector) where the central region between the two ends of the fragment is excised.
Figure 7:
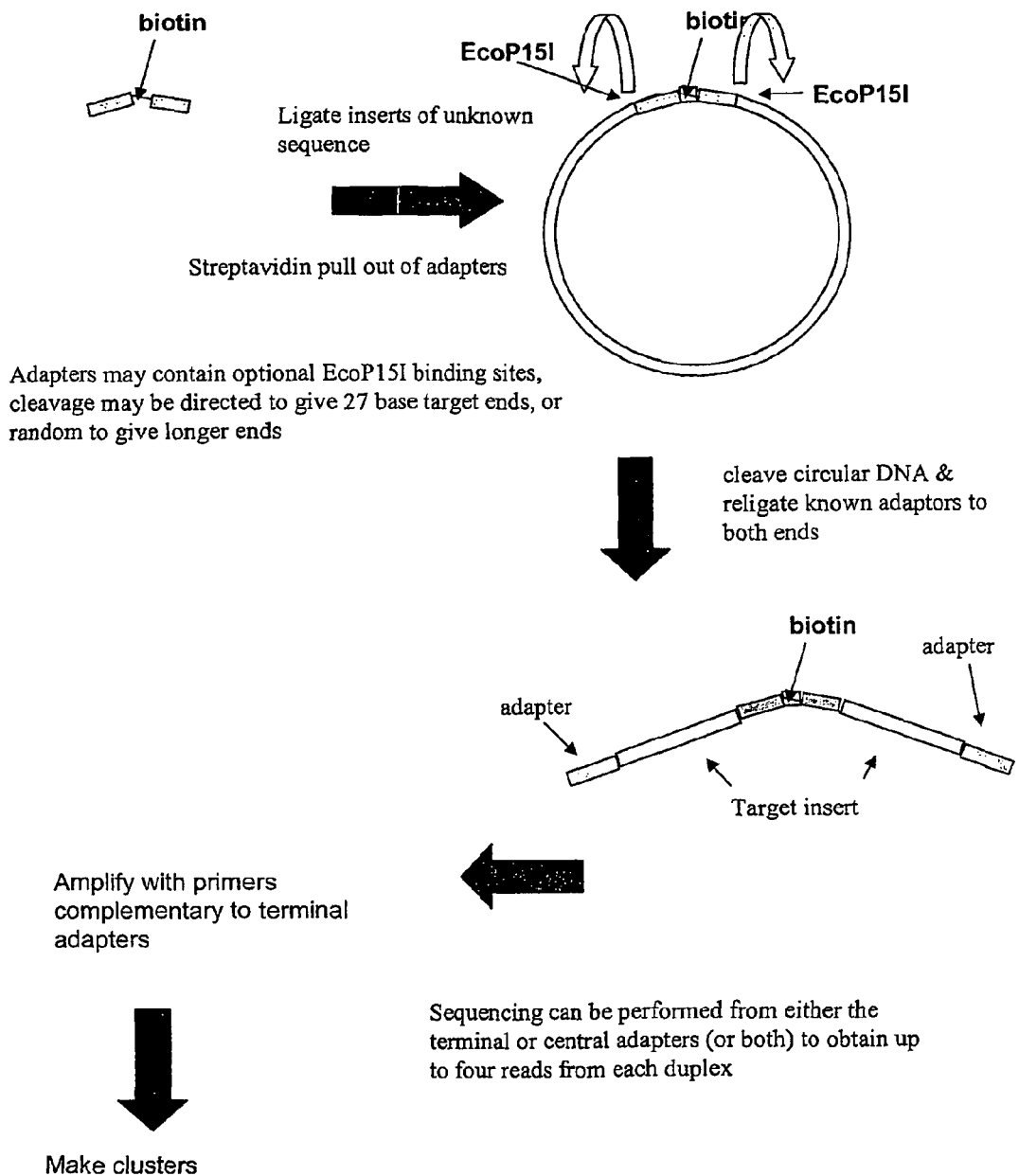
FIG. 7 shows a schematic of a method for preparing a sample to obtain a paired read from the two ends of a fragment of any length. The method uses a biotinylated adaptor to isolate circularised inserts containing the adaptor, the circles then being fragmented and treated such that the ends also comprise adaptors that allow subsequent amplification and sequencing.

The ends of each molecule can either be joined back together to make a single nucleotide 'ditag' sequence of type vector-target-target-vector, or an adaptor of known sequence can be used to act as a spacer region in a template of type vector-target-adaptor-target-vector, as shown in FIG. 4. An alternative way of building this type of construct is to open a circularised vector molecule and ligate adaptors onto each end, an example of which is shown in FIG. 7 where the fragmentation can be by the remote cutting restriction enzyme rather than the randomised method also covered in FIG. 7.

In the preparation of DNA templates for cluster production and SBS, two EcoP15I sites and other known adaptor sequences were attached to a circular vector with the target sequence in close proximity to the unknown target sequence, as shown in FIG. 4. The proximity of the EcoP15I sites to the target sequence allows cleavage at a specific position 27 by into the target sequence, thus allowing manipulation of 27 base sequences of the unknown target sequence. The use of two EcoP15I sites at either end of the target DNA fragment, allows the removal of the majority of the target sequence leaving two associated 27 by fragments at either end. A single sequencing read of 54 bases gives sequence information from the two ends of the original target, without the intervening bases. The construct of 54 contiguous bases is an example of a ditag, as it comprises the two 27 base pair ends of the original target connected together. This Ecop15 specific ditag construct comprises vector-target (27 bases)-target (27 bases)-vector. If the circular ditags are amplified with primers complementary to the vector regions, a linear ditag construct primer-target (27bases)-target (27 bases)-primer is obtained.

Religation to close a circular construct can be accomplished using sequences of any length sufficient to ensure efficient closure of the circle. Amplification using primers on either side of the original cut site will give copies of the desired polynucleotide template. However, the length of the unknown region that can be generated using such di-tag methods is limited by the availability of remote cutting restriction enzymes. Examples of the construction of such a library using restriction enzymes have been reported (Science 2005; Vol. 309. no. 5741, pp. 1728-1732).

Methods of producing ditags are well documented in, for example, WO00179553, WO03074734, WO06135342 or US2006/0024681. The amplification of single molecules of such ditags to produce a clustered array wherein both strands of each amplified duplex are immobilised, as taught for the first time by the present inventors, confers a significant advantage in that it is possible to simultaneously analyse a large number of ditags of different sequences on a single solid support. Moreover, inserting an adaptor into the ditag allows four sequencing reads from each template duplex rather than just two reads. Another significant limitation of prior art methods is the requirement to use restriction enzymes, which limit the length of the target sequences. The methods detailed herein which do not require the use of restriction enzymes provide a significant advantage in terms of the length of the two target fragments that can be sequenced.

An alternative approach with which to generate the desired constructs wherein the target polynucleotide fragments are longer than a restriction enzyme cut site, which are of particular advantage in the current invention, is to ligate a linear adaptor sequence into the unknown fragments to form a circular construct. A random shearing process such as sonication, nebulisation or exonuclease treatment can then be used to generate linear constructs containing a central adaptor sequence. The adaptors may be modified with groups such as biotin to aid purification of the adaptor-target circles or their fragments. End repair, followed by circularisation with another adaptor will generate a circular product with two known and two unknown regions. This can be amplified using pairs of primers to generate the desired known-unknown-known-unknown-known polynucleotide template. There are a number of variations on this technique, and the order of the steps is not fixed. It is anticipated that any technique used to generate a polynucleotide molecule containing known ends, and a known internal sequence between two unknown regions of interest for sequencing is encompassed within the scope of the current invention. A variety of methods that may be applicable to this type of sample preparation technique are shown in FIGS. 5, 6, 7, 9, 10 and 11. These methods are described below in reference to the figures.

Figure 5:
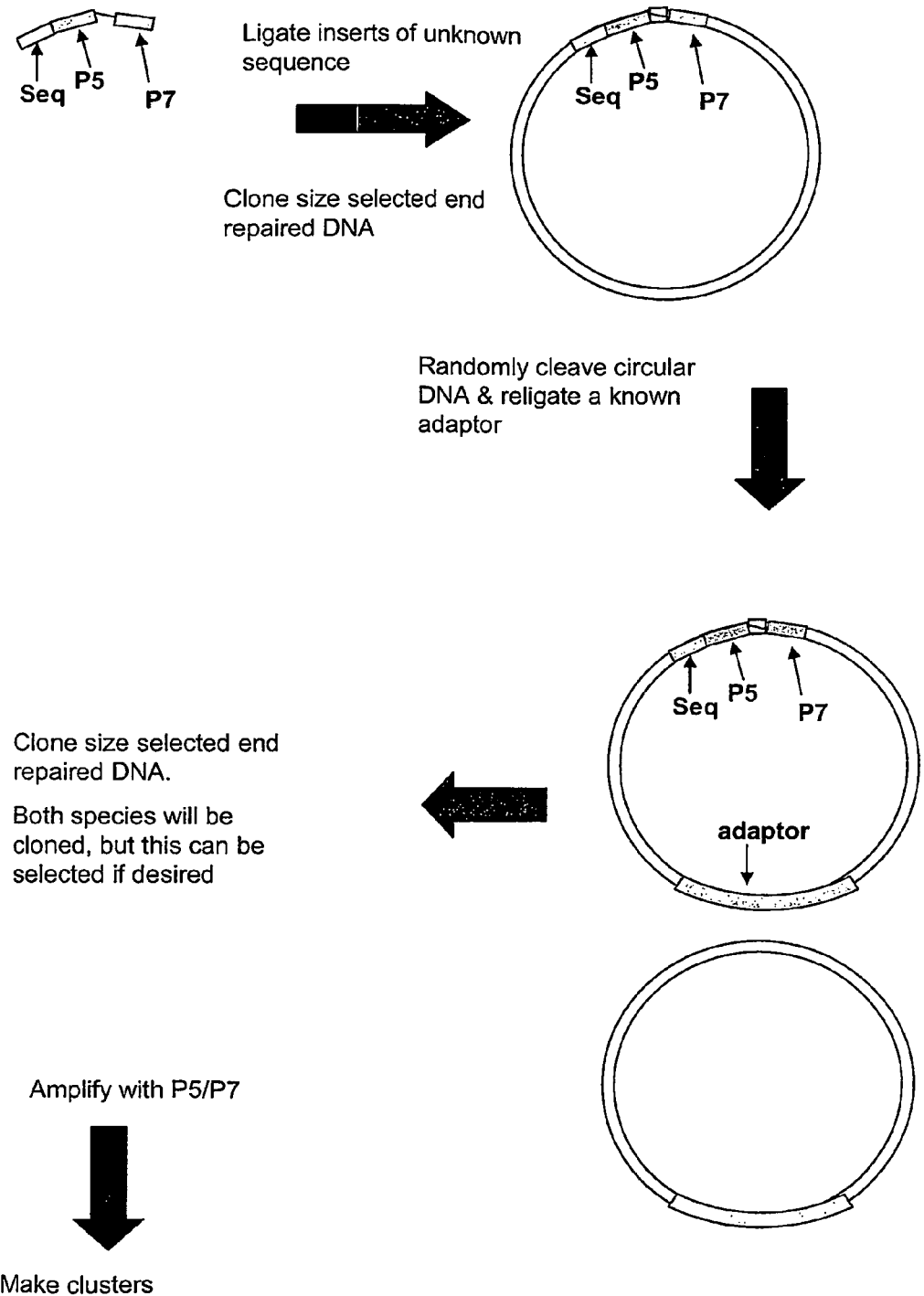
FIG. 5 shows a schematic of methods for determining paired reads of long unknown polynucleotide regions without using restriction enzymes.

FIG. 5 shows a schematic of methods for determining paired reads of long unknown polynucleotide regions without using restriction enzymes. The target inserts, can be, for example: PCR amplicons, randomly sheared nucleic acid samples isolated from biological samples (for example bacteria, viruses or other organisms), isolated clones, libraries of clones, plasmids, phosmids or any other source of nucleic acid that can be ligated into circles using suitable adaptors. The randomly sheared targets may be end repaired prior to ligation. If the sample is fragmented prior to ligation, then the fragments may be size selected into narrow distributions prior to ligation, or the fragmentation may be controlled to achieve fragments of a narrow size distribution atound a certain size, for example, 5 kb or 10 kb.

The circular constructs may be randomly fragmented, again using a variety of techniques such as sonication, nebulisation or hydroshearing. Due to the random nature of these processes, the fragments will be a mixture of those fragments that contain the adaptor sequence and those that do not. The fragmentation process may be less random if the adaptor is protected from fragmentation. Since the sequence of the adaptor region is known, this sequence may be used to selectively target DNA binding proteins or similar reagents to the adaptor region. If the proteins are of sufficient size, they will also bind the target sequence and protect the target from further fragmentation. The proteins could be targeted using the known sequence of the adaptor regions, for example using oligonucleotide-protein conjugates. It may be advantageous in such instances to use triplex forming oligonucleotides or molecules that can hybridise strongly to a duplex, such as peptide nucleic acid (PNA), that can strand invade into the duplex.

Suitable DNA binding proteins might include transcription factors, DNA polymerases or other nucleic acid modifying enzymes, chromatin or restriction enzymes, where the site of binding has been modified such that a cut is not possible. The size of the area protected depends on the method used to protect the target sequence, but may be from 20-200 bases from each end of the adaptor sequence.

The fragments can be re-circularised using a second adaptor to obtain essentially two types of circular constructs, those with only the second adaptor and those with both the first and second adaptors. Amplification of the circles with primers specific for the first adaptor will result in amplification of only those circles that contain the intact first adaptor sequence, and therefore only the desired products containing the construct primer-target-adaptor-target-primer will be obtained.

In all examples where circles are amplified, the amplification method may involve two primers as a standard amplification reaction, or may be performed by rolling circle amplification. In some instances two primers may be used in rolling circle amplification methods such that the initial copies of the circular templates are further amplified.

Figure 6:
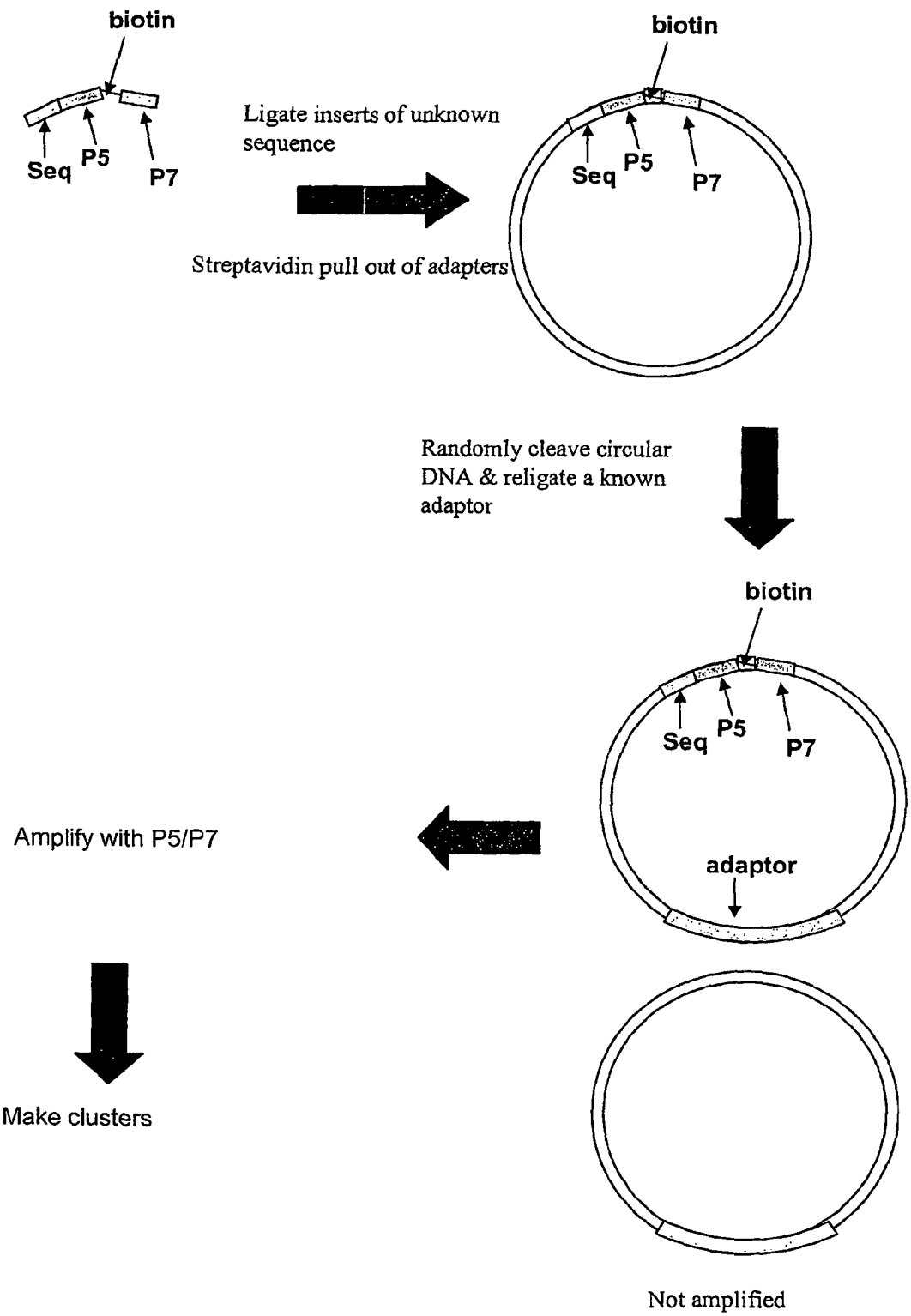
FIG. 6 shows a schematic of a method for preparing a sample to obtain a paired read from the two ends of a fragment of any length. The method uses a biotinylated adaptor to isolate circularised inserts comprising the adaptor. The circular inserts can then be cleaved and recircularised using a further adaptor into circles of smaller size containing two adaptor regions. The circles can be amplified using primers selective for the first adaptor to make a linear template suitable for amplification.

FIG. 6 shows a variation on FIG. 5 wherein the initial adaptors are biotinylated. Biotinylation of the adaptors allows some or all of the steps to be carried out on a solid support, or to purify the desired fragments when required. If the adaptors are ligated to the targets as described above, the non ligated target will not carry a biotin modification, so it can be readily removed from the mixture of molecules. Once the circles are fragmented, again the biotin group on the adaptor allows selection of the fragments that carry the initial adaptor over those that do not. The adaptor containing fragments can be ligated with a second adaptor as described above, and amplified with primers specific for the first adaptor sequence to make a linear template suitable for further amplification and/or sequencing.

FIG. 7 shows a variation on FIG. 6 wherein the fragmented circles are treated with adaptors such that both ends of the linear fragments are modified. This circumvents the need for a second circularisation reaction, whilst still allowing preparation of a construct of type adaptor-target-adaptor-target-adaptor.

Figure 9:
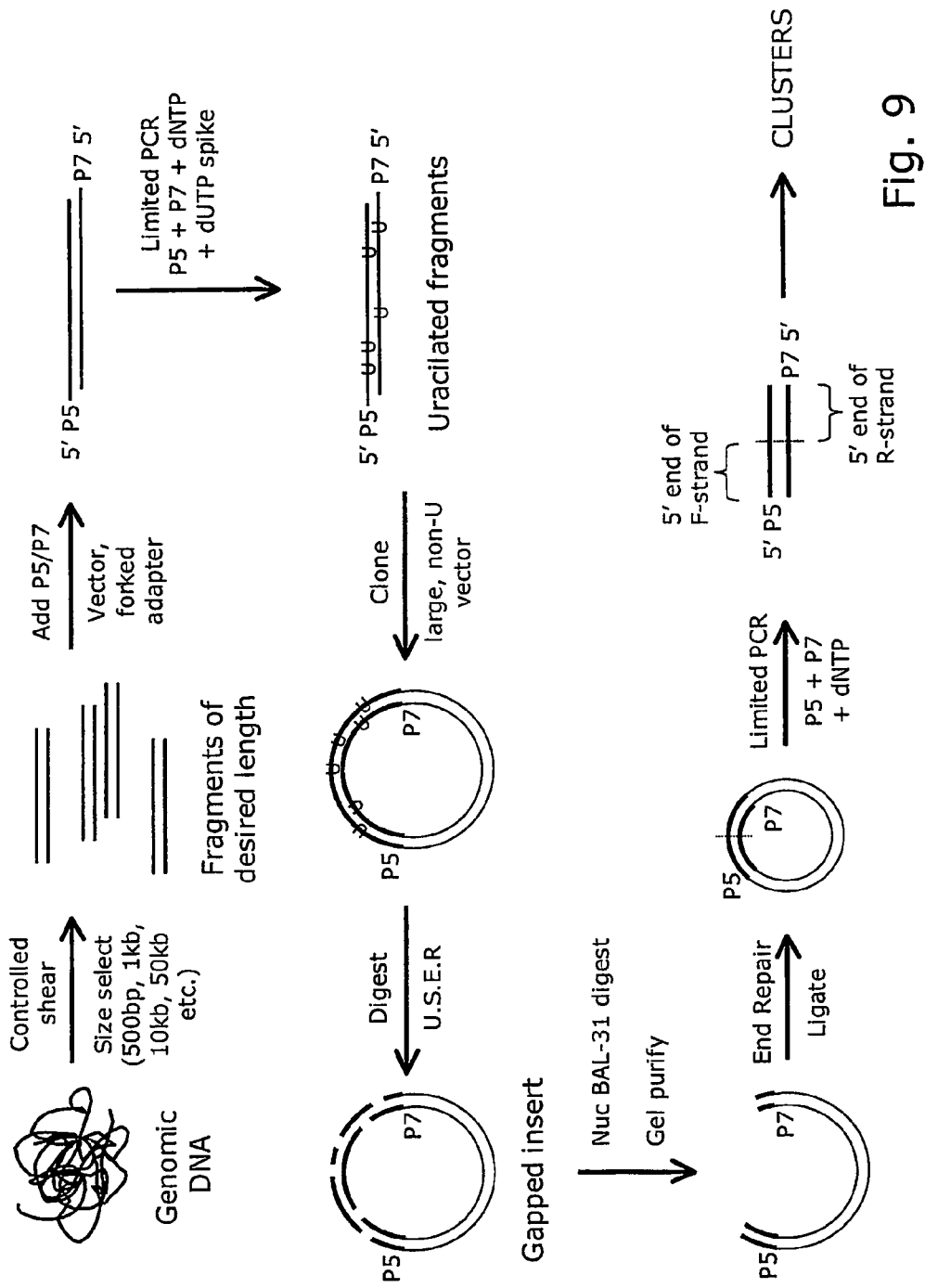
FIG. 9 shows a schematic for the preparation of a sample suitable for obtaining a pair of reads of a fragment of any length. The method is based on amplifying the fragments with a controlled amount of dUTP, thereby introducing a low level of modifications that allow the fragments to be randomly cut (i.e. cut where a uracil base is randomly inserted). The cut fragments can be religated into circles and amplified such that the two ends of the original PCR fragments are joined together with the central bases excised.

FIG. 9 shows a schematic for the preparation of a sample for obtaining a pair of reads from the distal ends of a fragment of any length. The method is based on amplifying the fragments with a controlled amount of dUTP, thereby introducing a low level of modifications that allow the fragments to be randomly cut (i.e. cut where a uracil base is randomly inserted). The cut fragments can be religated into circles and amplified such that the two ends of the original PCR fragments are joined together with the central bases excised.

Figure 10:
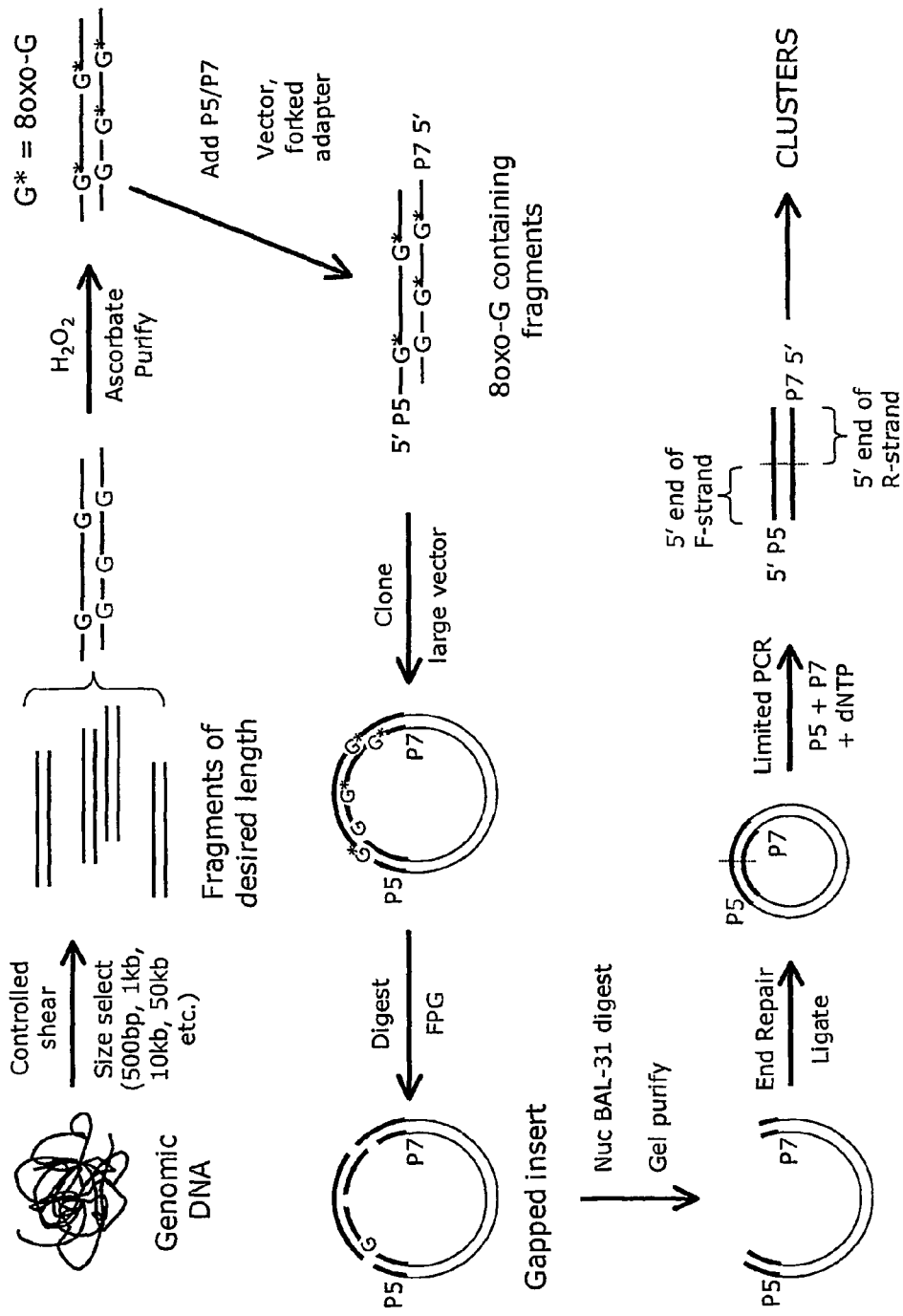
FIG. 10 shows a schematic for the preparation of a sample suitable for obtaining a pair of reads of a fragment of any length. The method is based on oxidising the guanine bases to a low level in the original sample, thereby introducing a low level of modifications that allow the fragments to be randomly cut (i.e. cut where a guanine base is randomly oxidised). The cut fragments can be religated into circles and amplified such that the two ends of the original PCR fragments are joined together with the central bases excised.

FIG. 10 shows a schematic for the preparation of a sample suitable for obtaining a pair of reads from the distal ends of a fragment of any length, without the need for an initial PCR reaction to introduce the modified bases needed for subsequent cleavage. The method is based on oxidising the guanine bases to a low level in the original sample, thereby introducing a low level of modifications that allow the fragments to be randomly cut (i.e. cut where a guanine base is randomly oxidised). The cut fragments can be religated into circles and amplified such that the two ends of the original PCR fragments are joined together with the central bases excised.

Figure 11:
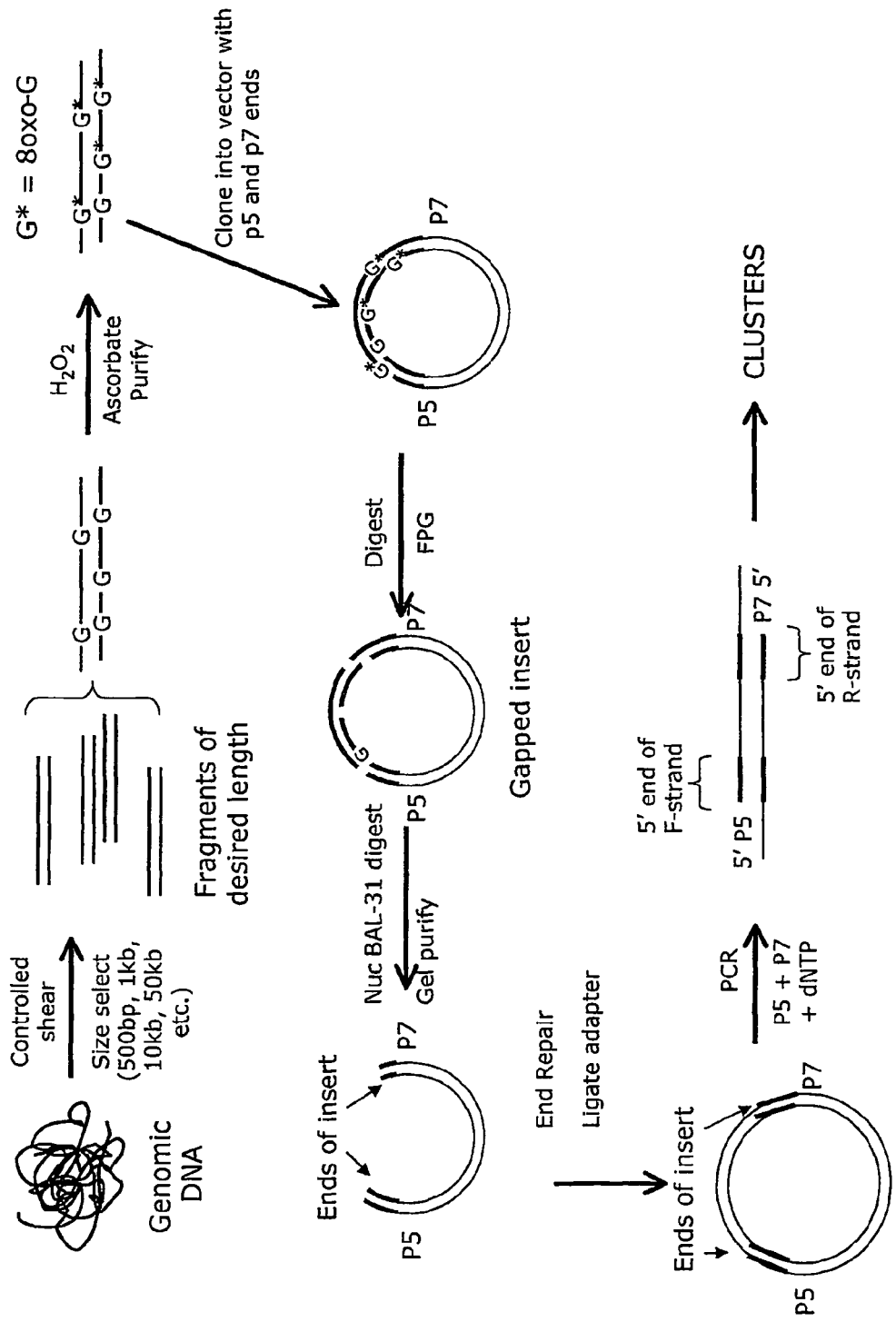
FIG. 11 shows a schematic for the preparation of a sample suitable for obtaining a pair of reads of a fragment of any length. The method is based on oxidising the guanine bases to a low level in the original sample, thereby introducing a low level of modifications that allow the fragments to be randomly cut (i.e. cut where a guanine base is randomly oxidised). If the vector-target ligated circles are cut open using an enzyme that removes the 8-oxo guanine bases, then only the ends of the target fragments remain attached to the vector. A new adaptor sequence can be attached to reclose the polished ends, producing a fragment with two known ends from the original vector, two ends from a target fragment and a central adaptor sequence. The fragment can be linearized by amplification using primers complementary to the ends of the original vector.

FIG. 11 shows a schematic for the preparation of a sample suitable for obtaining a pair of reads from the distal ends of a fragment of any length. The method is based on oxidising the guanine bases to a low level in the original sample, thereby introducing a low level of modifications that allow the fragments to be randomly cut (i.e. cut where a guanine base is randomly oxidised). If the vector-target ligated circles are cut open using an enzyme that removes the 8-oxo guanine bases, then only the ends of the target fragments will remain attached to the vector. A new adaptor sequence can be attached to re-circularize the polished ends, producing a fragment with two known ends from the original vector, two ends from a target fragment and a central adaptor sequence. The fragment can be linearized by amplification using primers complementary to the ends of the original vector to give a primer-target-adaptor-target-primer construct suitable for further amplification and/or sequencing.

Linearisation of Immobilised DNA

Polynucleotide molecules can be prepared to contain sequences for two sequencing primers as described above. If such molecules are immobilised such that one of the two immobilised ends can be cleaved from the surface, upon such cleavage the resulting double stranded DNA, which is now immobilised at only one end of the duplex, can be made single stranded using heat or chemical denaturing conditions to give a single stranded molecule containing two primer hybridisation sites. The process of removing all or a portion of one immobilised strand in a 'bridged' double-stranded nucleic acid structure may be referred to herein as 'linearisation'. The single stranded molecule can be sequenced using a first sequencing primer, which can then be removed and a second sequencing primer introduced to allow a second read. If the constructs are not linearised, then it is possible to obtain four reads from each duplex, since each strand can be sequenced twice, once from the 3' terminal adaptor sequence, and once from the central adaptor sequence.

To linearise the immobilised duplex strands, either the first or second strand of the template duplexes must include a cleavage site. Said cleavage site is a site which allows controlled cleavage of the first or second template strand by chemical, enzymatic or photochemical means. The double stranded polynucleotide is then only immobilised through one end. The polynucleotide is then denatured to leave a single stranded polynucleotide immobilised at the 5'-end. A first sequencing primer can then be hybridised to a single-stranded region of the template and used as the primer for a sequencing reaction, after which it is removed from the template, and a second sequencing primer is hybridised and used for sequencing of a different region of the single stranded template.

Any suitable enzymatic, chemical or photochemical cleavage reaction may be used to cleave. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulphide linkage with a reducing agent (e.g. TCEP), in which case the cleavage site should include an appropriate disulphide linkage; chemical cleavage of a diol linkage with periodate, in which case the cleavage site should include a diol linkage; generation of an abasic site and subsequent hydrolysis, etc.

In one embodiment cleavage may occur at a cleavage site in one or both strands of a template polynucleotide duplex which comprises one or more or any combination of non-natural nucleotides, ribonucleotides or a non-nucleotide chemical modifications.

Suitable cleavage techniques for use in the method of the invention are described in full in co-pending application WO07010251, and include, but are not limited to, the following:

i) Chemical Cleavage

The term "chemical cleavage" encompasses any method which utilises a non-nucleic acid and non-enzymatic chemical reagent in order to promote/achieve cleavage of one or both strands of a template polynucleotide duplex. If required, one or both strands of the template polynucleotide duplex may include one or more non-nucleotide chemical moieties and/or non-natural nucleotides and/or non-natural backbone linkages in order to permit chemical cleavage reaction. In a particular embodiment, the modification(s) required to permit chemical cleavage may be incorporated into an amplification primer used to form the template polynucleotide duplex by solid-phase nucleic acid amplification.

In a particular embodiment, one strand of the template polynucleotide duplex (or the amplification primer from which this strand is derived if formed by solid-phase amplification) may include a diol linkage which permits cleavage by treatment with periodate (e.g. sodium periodate). It will be appreciated that more than one diol can be included at the cleavage site.

Diol linker units based on phosphoamidite chemistry suitable for incorporation into polynucleotide chains are commercially available from Fidelity systems Inc. (Gaithersburg, Md., USA) or can be chemically prepared as described in WO07010251. One or more diol units may be incorporated into a polynucleotide using standard methods for automated chemical DNA synthesis. Hence, oligonucleotide primers including one or more diol linkers can be conveniently prepared by chemical synthesis.

In order to position the diol linker at an optimum distance from the solid support one or more spacer molecules may be included between the diol linker and the site of attachment to the solid support. To facilitate attachment to a solid support at the 5' end of the polynucleotide strand, the 5' end may be modified to include a phosphorothioate group. The phosphorothioate group can easily be attached during chemical synthesis of a "polynucleotide" chain including the spacer and diol units. The spacer molecules may include, for example, a stretch of nucleotides that are not complementary to the templates being amplified. Typically from 1 to 20, more particularly from 1 to 15 or from 1 to 10, and even more particularly 2, 3, 4, 5, 6, 7, 8, 9 or 10 spacer nucleotides may be included. In a particular embodiment, 10 spacer nucleotides are positioned between the point of attachment to the solid support and the diol linker. In another particular embodiment, polyT spacers are used, although other nucleotides and combinations thereof can be used. In another particular embodiment, the primer may include 10T spacer nucleotides.

The diol linker is cleaved by treatment with a "cleaving agent", which can be any substance which promotes cleavage of the diol. One such cleaving agent is periodate, for example aqueous sodium periodate ($NaIO_4$). Following treatment with the cleaving agent (e.g. periodate) to cleave the diol, the cleaved product may be treated with a "capping agent" in order to neutralise reactive species generated in the cleavage reaction. Suitable capping agents for this purpose include amines, such as ethanolamine or propanolamine (3-amino-propan-1-ol). Advantageously, the capping agent (e.g. propanolamine) may be included in a mixture with the cleaving agent (e.g. periodate) so that reactive species are capped as soon as they are formed.

The example of a combination of a diol linkage and cleaving agent (e.g. periodate) to achieve cleavage of at least one strand of a template polynucleotide duplex works well for linearisation of template duplexes on solid supported polyacrylamide hydrogels as treatment with periodate and propanolamine is compatible with nucleic acid integrity and with the chemistry of the hydrogel surface. Utility of diol linkages/periodate as a method of linearisation is not, however, limited to polyacrylamide hydrogel surfaces but also extends to linearisation of duplexes immobilised on other solid supports and surfaces, including supports coated with functionalised silanes (etc).

In a further embodiment, the strand to be cleaved (or the amplification primer from which this strand is derived if prepared by solid-phase amplification) may include a disulphide group which permits cleavage with a chemical reducing agent, e.g. Tris (2-carboxyethyl)-phosphate hydrochloride (TCEP).

ii) Cleavage of Abasic Sites

An "abasic site" is defined as a nucleotide position in a polynucleotide chain from which the base component has been removed. Abasic sites can occur naturally in DNA under physiological conditions by hydrolysis of nucleotide residues, but may also be formed chemically under artificial conditions or by the action of enzymes. Once formed, abasic sites may be cleaved (e.g. by treatment with an endonuclease or other single-stranded cleaving enzyme, exposure to heat or alkali), providing a means for site-specific cleavage of a polynucleotide strand.

In a particular, but non-limiting embodiment, an abasic site may be created at a pre-determined position on one strand of a template polynucleotide duplex and then cleaved by first incorporating deoxyuridine (U) at a pre-determined cleavage site in one strand of the template polynucleotide duplex. This can be achieved, for example, by including U in one of the primers used for preparation of the template polynucleotide duplex by solid-phase PCR amplification. The enzyme uracil DNA glycosylase (UDG) may then be used to remove the uracil base, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali.

Abasic sites may also be generated at non-natural/modified deoxyribonucleotides other than deoxyuridine and cleaved in an analogous manner by treatment with endonuclease, heat or alkali. For example, 8-oxoguanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV, AP lyase). If the non-natural/modified nucleotide is to be incorporated into an amplification primer for use in solid-phase amplification, then the non-natural/modified nucleotide should be capable of being copied by the polymerase used for the amplification reaction.

In one embodiment, the molecules to be cleaved may be exposed to a mixture containing the appropriate glycosylase and one or more suitable endonucleases. In such mixtures the glycosylase and the endonuclease will typically be present in an activity ratio of at least about 2:1.

This method of cleavage has particular advantages in relation to the creation of templates for nucleic acid sequencing. In particular, cleavage at an abasic site generated by treatment with a glycosylase such as UDG generates a free 3' hydroxyl group on the cleaved strand which can provide an initiation point for sequencing a region of the complementary strand. Moreover, if the initial double-stranded nucleic acid contains only one cleavable (e.g. uracil) base on one strand then a single "nick" can be generated at a unique position in this strand of the duplex. Since the cleavage reaction requires a residue, e.g. deoxyuridine, which does not occur naturally in DNA, but is otherwise independent of sequence context, if only one non-natural base is included there is no possibility of glycosylase-mediated cleavage occurring elsewhere at unwanted positions in the duplex. In contrast, were the double-stranded nucleic acid to be cleaved with a "nicking" endonuclease that recognises a specific sequence, there is a possibility that the enzyme may create nicks at "other" sites in the duplex (in addition to the desired cleavage site) if these possess the correct recognition sequence. This could present a problem if nicks are created in the strand it is intended to sequence rather than the strand that will be fully or partially removed to create the sequencing template and is a particular risk if the target portion of the double-stranded nucleic acid molecule is of unknown sequence.

The fact that there is no requirement for the non-natural (e.g. uracil) residue to be located in a detailed sequence context in order to provide a site for cleavage using this approach is itself advantageous. In particular, if the cleavage site is to be incorporated into an amplification primer to be used in the production of a clustered array by solid-phase amplification, it is necessarily only to replace one natural nucleotide (e.g. T) in the primer with a non-natural nucleotide (e.g. U) in order to enable cleavage. There is no need to engineer the primer to include a restriction enzyme recognition sequence of several nucleotides in length. Oligonucleotide primers including U nucleotides, and other non-natural nucleotides, such as those listed above, can easily be prepared using conventional techniques and apparatus for chemical synthesis of oligonucleotides.

Another advantage gained by cleavage of abasic sites in a double-stranded molecule generated by action of UDG on uracil is that the first base incorporated in a "sequencing-by-synthesis" reaction initiating at the free 3' hydroxyl group formed by cleavage at such a site will always be T. Hence, if the template polynucleotide duplex forms part of a clustered array comprised of many such molecules, all of which are cleaved in this manner to produce sequencing templates, then the first base universally incorporated across the whole array will be T. This can provide a sequence-independent assay for individual cluster intensity at the start of a sequencing "run".

iii) Cleavage of Ribonucleotides

Incorporation of one or more ribonucleotides into a polynucleotide strand which is otherwise comprised of deoxyribonucleotides (with or without additional non-nucleotide chemical moieties, non-natural bases or non-natural backbone linkages) can provide a site for cleavage using a chemical agent capable of selectively cleaving the phosphodiester bond between a deoxyribonucleotide and a ribonucleotide or using a ribonuclease (RNAse). Therefore, sequencing templates can be produced by cleavage of one strand of a template polynucleotide duplex at a site containing one or more consecutive ribonucleotides using such a chemical cleavage agent or an RNase. Particularly, the strand to be cleaved contains a single ribonucleotide to provide a site for chemical cleavage.

Suitable chemical cleavage agents capable of selectively cleaving the phosphodiester bond between a deoxyribonucleotide and a ribonucleotide include metal ions, for example rare-earth metal ions (especially $La^{3+}$, particularly $Tm^{3+}$, $Yb^{3+}$ or $Lu^{3+}$ (Chen et al. Biotechniques. 2002, 32: 518-520; Komiyama et al. Chem. Commun. 1999, 1443-1451)), Fe(3) or Cu(3), or exposure to elevated pH, e.g. treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions.

The base composition of the ribonucleotide(s) is generally not material, but can be selected in order to optimise chemical (or enzymatic) cleavage. By way of example, rUMP or rCMP may be used if cleavage is to be carried out by exposure to metal ions, especially rare earth metal ions.

The ribonucleotide(s) will typically be incorporated into one strand of a template polynucleotide duplex (or the amplification primer from which this strand is derived if prepared by solid-phase amplification), and may be situated in a region of the duplex which is single-stranded when the two complementary strands of the duplex are annealed (i.e. in a 5' overhanging portion). If the template polynucleotide duplex is prepared by solid-phase PCR amplification using forward and reverse amplification primers, one of which contains at least one ribonucleotide, the standard DNA polymerase enzymes used for PCR amplification are not capable of copying ribonucleotide templates. Hence, the PCR products will contain an overhanging 5' region comprising the ribonucleotide(s) and any remainder of the amplification primer upstream of the ribonucleotide(s).

The phosphodiester bond between a ribonucleotide and a deoxyribonucleotide, or between two ribonucleotides may also be cleaved by an RNase. Any endolytic ribonuclease of appropriate substrate specificity can be used for this purpose. If the ribonucleotide(s) are present in a region which is single-stranded when the two complementary strands of the double-stranded molecule are annealed (i.e. in a 5' overhanging portion), then the RNase will be an endonuclease which has specificity for single strands containing ribonucleotides. For cleavage with ribonuclease, two or more consecutive ribonucleotides may be included in a particular embodiment, and more particularly from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Polynucleotides incorporating one or more ribonucleotides can be readily synthesised using standard techniques for oligonucleotide chemical synthesis with appropriate ribonucleotide precursors. If the template polynucleotide duplex is prepared by solid-phase nucleic acid amplification, then it is convenient to incorporate one or more ribonucleotides into one of the primers to be used for the amplification reaction.

iv) Photochemical Cleavage

The term "photochemical cleavage" encompasses any method which utilises light energy in order to achieve cleavage of one or both strands of the double-stranded nucleic acid molecule.

A site for photochemical cleavage can be provided by a non-nucleotide chemical spacer unit in one of the strands of the double-stranded molecule (or the amplification primer from which this strand is derived if prepared by solid-phase amplification). Suitable photochemical cleavable spacers include the PC spacer phosphoamidite (4-(4,4'-Dimethoxytrityloxy)butyramidomethyl)-1-(2-nitrophenyl)-ethyl]-2-cyanoethyl-(N,N-diisopropyl)-phosphoramidite) supplied by Glen Research, Sterling, Va., USA (cat number 10-4913-XX) which has the structure:

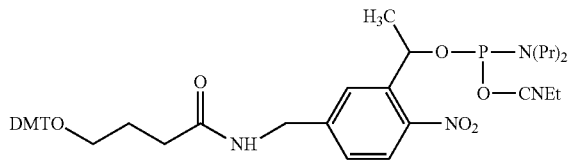

The spacer unit can be cleaved by exposure to a UV light source.

This spacer unit can be attached to the 5' end of a polynucleotide, together with a thiophosphate group which permits attachment to a solid surface, using standard techniques for chemical synthesis of oligonucleotides. Conveniently, this spacer unit can be incorporated into a forward or reverse amplification primer to be used for synthesis of a photocleavable template polynucleotide duplex by solid-phase amplification.

v) Cleavage of Hemimethylated DNA

Site-specific cleavage of one strand of a double-stranded nucleic acid molecule may also be achieved by incorporating one or more methylated nucleotides into this strand and then cleaving with an endonuclease enzyme specific for a recognition sequence including the methylated nucleotide(s).

The methylated nucleotide(s) will typically be incorporated in a region of one strand of the template polynucleotide duplex having a complementary stretch of non-methylated deoxyribonucleotides on the complementary strand, such that annealing of the two strands produces a hemimethylated duplex structure. The hemimethylated duplex may then be cleaved by the action of a suitable endonuclease. For the avoidance of doubt, enzymes which cleave such hemimethylated target sequences are not to be considered as "restriction endonucleases" excluded from the scope of the second aspect of the invention, but rather are intended to form part of the subject-matter of the invention.

Polynucleotides incorporating one or methylated nucleotides may be prepared using standard techniques for automated DNA synthesis, using appropriately methylated nucleotide precursors. If the template polynucleotide duplex is prepared by solid-phase nucleic acid amplification, then it is convenient to incorporate one or more methylated nucleotides into one of the primers to be used for the amplification reaction.

vi) PCR Stoppers

In another embodiment of the invention the template polynucleotide duplex may be prepared by solid-phase amplification using forward and reverse primers, one of which contains a "PCR stopper". A "PCR stopper" is any moiety (nucleotide or non-nucleotide) which prevents read-through of the polymerase used for amplification, such that it cannot extend/copy beyond that point. The result is that amplified strands derived by extension of the primer containing the PCR stopper will contain a 5' overhanging portion. This 5' overhang (other than the PCR stopper itself) may be comprised of naturally occurring deoxyribonucleotides, with predominantly natural backbone linkages, i.e. it may simply be a stretch of single-stranded DNA. The molecule may then be cleaved in the 5' overhanging region with the use of a cleavage reagent (e.g. an enzyme) which is selective for cleavage of single-stranded DNA but not double stranded DNA, for example mung bean nuclease.

The PCR stopper may be essentially any moiety which prevents read-through of the polymerase to be used for the amplification reaction. Suitable PCR stoppers include, but are not limited to, hexaethylene glycol (HEG), abasic sites, and any non-natural or modified nucleotide which prevents read-through of the polymerase, including DNA analogues such as peptide nucleic acid (PNA).

Stable abasic sites can be introduced during chemical oligonucleotide synthesis using appropriate spacer units containing the stable abasic site. By way of example, abasic furan (5'-O-Dimethoxytrityl-1',2'-Dideoxyribose-3'-[(2-cyanoethyl)-(N,N-diisopropyl)]-phosphoramidite) spacers commercially available from Glen Research, Sterling, Va., USA, can be incorporated during chemical oligonucleotide synthesis in order to introduce an abasic site. Such a site can thus readily be introduced into an oligonucleotide primer to be used in solid-phase amplification. If an abasic site is incorporated into either forward or reverse amplification primer the resulting amplification product will have a 5' overhang on one strand which will include the abasic site (in single-stranded form). The single-stranded abasic site may then be cleaved by the action of a suitable chemical agent (e.g. exposure to alkali) or an enzyme (e.g. AP-endonuclease VI, Shida et al. Nucleic Acids Research, 1996, Vol. 24, 4572-4576).

vii) Cleavage of Peptide Linker

A cleavage site can also be introduced into one strand of a template polynucleotide duplex by preparing a conjugate structure in which a peptide molecule is linked to one strand of the duplex (or the amplification primer from which this strand is derived if prepared by solid-phase amplification). The peptide molecule can subsequently be cleaved by a peptidase enzyme of the appropriate specificity, or any other suitable means of non-enzymatic chemical or photochemical cleavage. Typically, the conjugate between peptide and nucleic acid will be formed by covalently linking a peptide to one strand only of the template polynucleotide duplex, with the peptide portion being conjugated to the 5' end of this strand, adjacent to the point of attachment to the solid surface. If the template polynucleotide duplex is prepared by solid-phase amplification, the peptide conjugate may be incorporated at the 5' end of one of the amplification primers. Obviously the peptide component of this primer will not be copied during PCR amplification, hence the "bridged" amplification product will include a cleavable 5' peptide "overhang" on one strand.

Conjugates between peptides and nucleic acids wherein the peptide is conjugated to the 5' end of the nucleic acid can be prepared using techniques generally known in the art. In one such technique the peptide and nucleic acid components of the desired amino acid and nucleotide sequence can be synthesised separately, e.g. by standard automated chemical synthesis techniques, and then conjugated in aqueous/organic solution. By way of example, the OPeC™ system commercially available from Glen Research is based on the "native ligation" of an N-terminal thioester-functionalized peptide to a 5'-cysteinyl oligonucleotide. Pentafluorophenyl S-benzylthiosuccinate is used in the final coupling step in standard Fmoc-based solid-phase peptide assembly. Deprotection with trifluoroacetic acid generates, in solution, peptides substituted with an N-terminal S-benzylthiosuccinyl group. O-trans-4-(N-a-Fmoc-S-tert-butylsulfenyl-l-cysteinyl) aminocyclohexyl O-2-cyanoethyl-N,N-diisopropylphosphoramidite is used in the final coupling step in standard phosphoramidite solid-phase oligonucleotide assembly. Deprotection with aqueous ammonia solution generates in solution 5'-S-tert-butylsulfenyl-L-cysteinyl functionalized oligonucleotides. The thiobenzyl terminus of the Modified Peptide is converted to the thiophenyl analogue by the use of thiophenol, whilst the Modified Oligonucleotide is reduced using tris(carboxyethyl)-phosphine. Coupling of these two intermediates, followed by the "native ligation" step, leads to formation of the Oligonucleotide-Peptide Conjugate.

The conjugate strand containing peptide and nucleic acid can be covalently attached to a solid support using any suitable covalent linkage technique known in the art which is compatible with the chosen surface. If the peptide/nucleic acid conjugate structure is an amplification primer to be used for solid-phase PCR amplification, attachment to the solid support must leave the 3' end of the nucleic acid component free.

The peptide component can be designed to be cleavable by any chosen peptidase enzyme, of which many are known in the art. The nature of the peptidase is not particularly limited, it is necessary only for the peptidase to cleave somewhere in the peptide component. Similarly, the length and amino acid sequence of the peptide component is not particularly limited except by the need to be "cleavable" by the chosen peptidase.

The length and precise sequence of the nucleic acid component is also not particularly limited, it may be of any desired sequence. If the nucleic acid component is to function as a primer in solid-phase PCR, then its length and nucleotide sequence will be selected to enable annealing to the template to be amplified.

Enzymatic Digestion with Restriction Endonuclease/Nicking Endonuclease

Cleavage of double-stranded polynucleotides with restriction endonuclease is a technique in routine use in the art of molecular biology. Nicking endonucleases are enzymes that selectively cleave or "nick" one strand of a polynucleotide duplex and are also well known in the art of molecular biology. The invention is not limited with respect to the nature of the enzyme. Essentially any restriction or nicking endonuclease may be used, provided that a suitable recognition sequence can be included at the cleavage site.

The method of the invention is described in further detail as follows.

Any suitable solid support and any suitable attachment means known in the art may be used, of which several are described by way of example below. Linkage to the solid support may be achieved via covalent attachment.

The polynucleotide duplexes will typically be formed from two complementary polynucleotide strands comprised of deoxyribonucleotides joined by phosphodiester bonds, but may additionally include one or more ribonucleotides and/or non-nucleotide chemical moieties and/or non-naturally occurring nucleotides and/or non-naturally occurring backbone linkages. In particular, the double-stranded nucleic acid may include non-nucleotide chemical moieties, e.g. linkers or spacers, at the 5' end of one or both strands. By way of non-limiting example, the double-stranded nucleic acid may include methylated nucleotides, uracil bases, phosphorothioate groups, ribonucleotides, diol linkages, disulphide linkages, peptides etc. Such non-DNA or non-natural modifications may be included in order to permit cleavage, or to confer some other desirable property, for example to enable covalent attachment to a solid support, or to act as spacers to position a site of cleavage an optimal distance from the solid support.

The template duplexes may also include non-target sequences at both the 5' and 3' ends, flanking the target polynucleotide. If the template duplexes are formed by solid-phase amplification, these non-target sequences will generally be derived from the primers used for solid-phase amplification.

The polynucleotide duplexes form part of a single cluster or colony comprised of many such first and second duplexes, and the cluster or colony will itself typically form part of an array of many such clusters or colonies. The terms "cluster" and "colony" are used interchangeably throughout and refer to a discrete site on a solid support comprised of a plurality of identical immobilised nucleic acid strands and a plurality of identical immobilised complementary nucleic acid strands. The term "clustered array" refers to an array formed from such clusters or colonies.

A key feature of the invention is that both sequencing runs can occur in the same cluster or colony on a clustered array. On such an array each duplex within each colony will comprise the same double-stranded target polynucleotide, whereas different colonies may be formed of duplexes comprising different double-stranded target polynucleotides. In a particular embodiment at least 90%, more particularly at least 95% of the colonies on a given clustered array will be formed from template duplexes comprising different double-stranded target polynucleotides, although within each individual colony on the array all template duplexes will comprise the same double-stranded target polynucleotide.

The amplified polynucleotides can then be treated in such a way to allow primer hybridisation. This can be performed either by heating the amplified clusters to denature the duplexes, followed by cooling in the presence of the first sequencing primer, by a chemical treatment such as sodium hydroxide to denature the duplexes or by a treatment to cleave one or both of the strands of the duplex polynucleotide.

Each polynucleotide duplex on the array contains the same universal primer recognition regions to allow the same primers to be used to sequence every cluster. A first sequencing primer is then hybridised to the first template strand and a sequencing reaction proceeds via successive incorporation of nucleotides to the first sequencing primer, resulting in determination of the sequence of a first region of the target polynucleotide.

Hybridisation of sequencing primer to the template strand is achieved by contacting the primer and template strand under conditions which promote annealing of primer to template. Such conditions will generally be well known to those skilled in the art of molecular biology.

When the first sequencing reaction is complete, the extended first sequencing primer is removed from the surface. This can be achieved by heating, or chemical denaturation. A second sequencing primer is then hybridised to a second region of the template and a sequencing reaction proceeds via successive addition of nucleotides to the second sequencing primer, resulting in determination of the sequence of a second region of the target polynucleotide.

Sequencing can be carried out using any suitable "sequencing-by-synthesis" technique, wherein nucleotides are added successively to a free 3' hydroxyl group, typically provided by annealing of a sequencing primer, resulting in synthesis of a polynucleotide chain in the 5' to 3' direction. In a particular embodiment, the nature of the nucleotide added is determined after each addition.

One particular sequencing method which can be used in the methods of the invention relies on the use of modified nucleotides that can act as reversible chain terminators. Nucleotides for use in the invention are described fully in WO04018497 and U.S. Pat. No. 7,057,026. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single, experiment if each of the modified nucleotides has attached thereto a different label, known to correspond to the particular base, which facilitates discrimination between the bases added at each incorporation step. Alternatively, a separate reaction may be carried out containing each of the modified nuceotides, which are added separately.

The modified nucleotides may carry a label to facilitate their detection. In a particular embodiment, the label is a fluorescent label. Each nucleotide type may carry a different fluorescent label. Fluorescent labels suitable for use in the current invention are described in U.S. application 60/801, 270. However the detectable label need not be a fluorescent label. Any label can be used which allows the detection of the incorporation of the nucleotide into the DNA sequence.

One method for detecting the fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. An imaging system suitable for determining the fluorescent signal from incorporated nucleotides is described in application No. 60/788,248.

The methods of the invention are not limited to use of the sequencing method outlined above, but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing) and sequencing by ligation-based methods, for example as described in U.S. Pat. No. 6,306,597.

The target double-stranded polynucleotide to be sequenced using the method of the invention may be any polynucleotide that it is desired to sequence. The target polynucleotide may be of known, unknown or partially known sequence, such as, for example in re-sequencing applications. Using the template preparation method described in detail below it is possible to prepare arrays of templates starting from essentially any double-stranded target polynucleotide of known, unknown or partially known sequence. With the use of arrays it is possible to sequence multiple targets of the same or different sequence in parallel. A particular application of the pairwise method is in the sequencing of fragments of genomic DNA. The method provides particular advantages in the identification of genome rearrangements, since the two regions of sequence obtained for each target molecule using the method will be known to be linked within a certain distance of each other in the genome, depending on the size of the starting target molecule.

Preparation of Templates to be Sequenced

Suitable templates for sequencing using the method of the invention can be prepared by solid-phase nucleic acid amplification to produce nucleic acid colonies. This can be done using procedures analogous to those described in WO 98/44151 and WO 00/18957, the contents of which are incorporated herein in their entirety by reference.

For amplification to proceed, a mixture of two amplification primers is immobilised or "grafted" onto the surface of a suitable solid support.

The amplification primers are oligonucleotide molecules having the following structures:

```
Forward primer: A-L-X-S1

Reverse primer: A-L-Y-S2
```

Wherein A represents a moiety which allows attachment to the solid support, L is an optional linker moiety, X is an optional cleavage site and S1 and S2 are polynucleotide sequences which permit amplification of a template nucleic acid molecule comprising the target double-stranded polynucleotide.

The mixture of primers will generally comprise substantially equal amounts the forward and reverse primers.

L represents a linker which may be included but is not strictly necessary. The linker may be a carbon-containing chain such as those of formula $(CH_2)_n$ wherein "n" is from 1 to about 1500, for example less than about 1000, particularly less than 100, e.g. from 2-50, particularly 5-25. However, a variety of other linkers may be employed with the only restriction placed on their structures being that the linkers are stable under conditions under which the polynucleotides are intended to be used subsequently, e.g. conditions used in DNA amplification and sequencing.

Linkers which do not consist of only carbon atoms may also be used. Such linkers include polyethylene glycol (PEG) having a general formula of $(CH_2—CH_2—O)_m$, wherein m is from about 1 to 600, particularly less than about 500.

Linkers formed primarily from chains of carbon atoms and from PEG may be modified so as to contain functional groups which interrupt the chains. Examples of such groups include ketones, esters, amines, amides, ethers, thioethers, sulfoxides, sulfones. Separately or in combination with the presence of such functional groups may be employed alkene, alkyne, aromatic or heteroaromatic moieties, or cyclic aliphatic moieties (e.g. cyclohexyl). Cyclohexyl or phenyl rings may, for example, be connected to a PEG or $(CH_2)_n$ chain through their 1- and 4-positions.

As an alternative to the linkers described above, which are primarily based on linear chains of saturated carbon atoms, optionally interrupted with unsaturated carbon atoms or heteroatoms, other linkers may be envisaged which are based on nucleic acids or monosaccharide units (e.g. dextrose). It is also within the scope of this invention to utilise peptides as linkers.

In a further embodiment linker may comprise one or more nucleotides which form part of the amplification primer but which do not participate in any reaction carried out on or with the primer (e.g. a hybridisation or amplification reaction). Such nucleotides may also be referred to herein as "spacer" polynucleotides. Typically from 1 to 20, more particularly from 1 to 15 or from 1 to 10, and more particularly 2, 3, 4, 5, 6, 7, 8, 9 or 10 spacer nucleotides may be included. Most particularly the primer will include 10 spacer nucleotides. PolyT spacers may be used, although other nucleotides and combinations thereof can also be used. In one particular embodiment the primer may include 10T spacer nucleotides.

The one or more spacer nucleotides function to space the portion of the primer required to hybridise to a target and direct amplification, away from the site of attachment to the solid support (i.e. S1 or S2). The inclusion of spacer nucleotides at the 5' end can markedly improve the performance of hybridisation of complementary polynucleotides to region S1 or S2. In a particular embodiment the polynucleotide will include 10T spacer nucleotides and a 5' phosphorothioate group for attachment to the solid support (moiety A), although other attachment moieties may be used as discussed below.

Sequences S1 and S2 in the forward and reverse primers are polynucleotide sequences which, in combination, direct amplification of a template by solid-phase bridging amplification reaction. The template to be amplified must itself comprise (when viewed as a single strand) at the 3' end a sequence capable of hybridising to sequence S1 in the forward primers and at the 5' end a sequence the complement of which is capable of hybridising to sequence S2 the reverse primer.

The precise nature of sequences S1 and S2 in the forward and reverse primer oligonucleotides will be dependent on the nature of the template it is intended to amplify. S1 and S2 must be capable of hybridising to cognate sequences on complementary strands of the template to be amplified. The term "hybridisation" encompasses sequence-specific binding between primer and template. Binding of a primer to its cognate sequence in the template should occur under typical conditions used for primer-template annealing in standard PCR. Typically hybridisation conditions are 5×SSC at 40° C., following an initial denaturation step. It is not essential for hybridisation that sequences S1 and S2 be exactly complementary to their cognate sequences in the template to be amplified.

S1 and S2 may be of different or identical sequence and will typically be around 20-30 nucleotides in length. The primers can include natural and non-natural DNA bases, also ribonucleotides or any combination thereof, and may also include non-natural backbone linkages such as disulphides or phosphorothioates.

Cleavage site X may fall within sequence S1 or S2, or if the linker L is itself a polynucleotide cleavage they may form part of linker region L. In other embodiments the cleavage site may be formed at the junction of sequences L and S1 or L and S2, or at the junction between moiety A and linker L (if present) or between moiety A and sequence S1 or S2 (if L not present).

Moiety A may be any chemical moiety which permits immobilisation of an oligonucleotide primer on a solid support. The surface of the solid support may itself be functionalised to permit attachment of the primers. Any suitable covalent or non-covalent attachment means may be used, of which many are known in the art.

By way of example, biotinylated albumins (BSA) can form a stable attachment of biotin groups by physisorption of the protein onto surfaces. Covalent modification can also be performed using silanes, which have been used to attach molecules to a solid support, usually a glass slide. By way of example, a mixture of tetraethoxysilane and triethoxy-bromoacetamidopropyl-silane (e.g. in a ratio of 1:100) can be used to prepare functionalised glass slides which permit attachment of molecules nucleic acids including a thiophosphate or phosphorothioate functionality. Biotin molecules can be attached to surfaces using appropriately reactive species such as biotin-PEG-succinimidyl ester which reacts with an amino surface. A mixture of amplification primers may then be brought into contact with the functionalised solid support.

In alternative embodiments functionalised polyacrylamide hydrogels may be used to attach primers wherein moiety A is a sulfur-containing nucleophilic groups are used. Examples of appropriate sulfur nucleophile-containing polynucleotides are disclosed in Zhao et al (*Nucleic Acids Research,* 2001, 29(4), 955-959) and Pirrung et al (*Langmuir,* 2000, 16, 2185-2191) and include, for example, simple thiols, thiophosphates and thiophosphoramidates. Particular hydrogels are those formed from a mixture of (i) a first comonomer which is acrylamide, methacrylamide, hydroxyethyl methacrylate or N-vinyl pyrrolidinone; and (ii) a second comonomer which is a functionalised acrylamide or acrylate of formula (I):

$$H_2C=C(H)—C(=O)\text{-A-B—C} \qquad (I);$$

or a methacrylate or methacrylamide of formula (II):

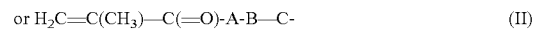

$$\text{or } H_2C=C(CH_3)—C(=O)\text{-A-B—C-} \qquad (II)$$

(wherein:

A is NR or O, wherein R is hydrogen or an optionally substituted saturated hydrocarbyl group comprising 1 to 5 carbon atoms;

—B— is an optionally substituted alkylene biradical of formula —$(CH_2)_n$— wherein n is an integer from 1 to 50; and wherein n=2 or more, one or more optionally substituted ethylene biradicals —$CH_2CH_2$— of said alkylene biradical may be independently replaced by ethenylene and ethynylene moieties; and wherein n=1 or more, one or more methylene biradicals —$CH_2$— may be replaced independently with an optionally substituted mono- or polycyclic hydrocarbon biradical comprising from 4 to 50 carbon atoms, or a corresponding heteromonocyclic or heteropolycyclic biradical wherein at least 1 $CH_2$ or $CH_2$ is substituted by an oxygen sulfur or nitrogen atom or an NH group; and C is a group for reaction with a compound to bind the compound covalently to the hydrogel) to form a polymerised product. A particular hydrogel is formed by co-polymerisation of acrylamide and N-(5-bromoacetamidylpentyl)acrylamide (BRAPA).

The term "solid support", as used herein, refers to the material to which the polynucleotides molecules are attached. Suitable solid supports are available commercially, and will be apparent to the skilled person. The supports can be manufactured from materials such as glass, ceramics, silica and silicon. Supports with a gold surface may also be used. The supports usually comprise a flat (planar) surface, or at least a structure in which the polynucleotides to be interrogated are in approximately the same plane. Alternatively, the solid support can be non-planar, e.g., a microbead. Any suitable size may be used. For example, the supports might be on the order of 1-10 cm in each direction.

For the grafting reaction to proceed a mixture of the amplification primers is applied to a (suitable functionalised) solid support under conditions which permit reaction between moiety A and the support. The result of the grafting reaction is a substantially even distribution of the primers over the solid support.

In certain embodiments the template to be amplified may be grafted onto the solid support together with the amplification primers in a single grafting reaction. This can be achieved by adding template molecules including moiety A at the 5' end to the mixture of primers to form a primer-template mixture. This mixture is then grafted onto the solid support in a single step. Amplification may then proceed using the immobilised template and primers in a reaction analogous to that described in WO 00/18957. The first step in such a reaction will be hybridisation between surface-bound templates and surface-bound amplification primers.

If the mixture of primers only is grafted onto the solid support and the template to be amplified is present in free solution, the amplification reaction may proceed substantially as described in WO 98/44151. Briefly, following attachment of the primers the solid support is contacted with the template to be amplified under conditions which permit hybridisation between the template and the immobilised primers. The template is usually added in free solution under suitable hybridisation conditions, which will be apparent to the skilled reader. Typically hybridisation conditions are, for example, 5×SSC at 40° C., following an initial denaturation step. Solid-phase amplification can then proceed, the first step of the amplification being a primer extension step in which nucleotides are added to the 3' end of the immobilised primer hybridised to the template to produce a fully extended complementary strand. This complementary strand will thus include at its 3' end a sequence which is capable of binding to the second primer molecule immobilised on the solid support. Further rounds of amplification (analogous to a standard PCR reaction) lead to the formation of clusters or colonies of template molecules bound to the solid support.

Sequences S1 and S2 in the amplification primers may be specific for a particular target nucleic acid that it is desired to amplify, but in other embodiments sequences S1 and S2 may be "universal" primer sequences which enable amplification of any target nucleic acid of known or unknown sequence which has been modified to enable amplification with the universal primers.

Suitable templates to be amplified with universal primers may be prepared by modifying target double-stranded polynucleotides by addition of known adaptor sequences to the 5' and 3' ends of the target nucleic acid molecules to be amplified. The target molecules themselves may be any double-stranded molecules it is desired to sequence (e.g. random fragments of human genomic DNA). The adaptor sequences enable amplification of these molecules on a solid support to form clusters using forward and reverse primers having the general structure described above, wherein sequences S1 and S2 are universal primer sequences.

The adaptors are typically short oligonucleotides that may be synthesised by conventional means. The adaptors may be attached to the 5' and 3' ends of target nucleic acid fragments by a variety of means (e.g. subcloning, ligation. etc). More specifically, two different adaptor sequences are attached to a target nucleic acid molecule to be amplified such that one adaptor is attached at one end of the target nucleic acid molecule and another adaptor is attached at the other end of the target nucleic acid molecule. The resultant construct comprising a target nucleic acid sequence flanked by adaptors may be referred to herein as a "template nucleic acid construct".

The target double-stranded polynucleotides may advantageously be size-fractionated prior to modification with the adaptor sequences.

The adaptors contain sequences which permit nucleic acid amplification using the amplification primer molecules immobilised on the solid support. These sequences in the adaptors may be referred to herein as "primer binding sequences". In order to act as a template for nucleic acid amplification, a single strand of the template construct must contain a sequence which is complementary to sequence S1 in the forward amplification primers (such that the forward primer molecule can bind and prime synthesis of a complementary strand) and a sequence which corresponds to sequence S2 in the reverse amplification primer molecules (such that the reverse primer molecule can bind to the complementary strand). The sequences in the adaptors which permit hybridisation to primer molecules will typically be around 20-30 nucleotides in length, although the invention is not limited to sequences of this length.

The precise identity of sequences S1 and S2 in the amplification primers, and hence the cognate sequences in the adaptors, are generally not material to the invention, as long as the primer molecules are able to interact with the amplification sequences in order to direct bridging amplification. The criteria for design of primers are generally well known to those of ordinary skill in the art.

Solid-phase amplification by either the method analogous to that of WO 98/44151 or that of WO 00/18957 will result in production of an array of colonies of "bridged" amplification products. Both strands of the amplification product will be immobilised on the solid support at or near the 5' end, this attachment being derived from the original attachment of the amplification primers. Typically the amplification products within each colony will be derived from amplification of a single target molecule.

The utility of the sequencing method of the invention is not limited to sequencing of templates produced by an amplification reaction. The method may be applied to sequencing of double-stranded templates immobilised on a support by any other means amenable to repeated cycles of hybridisation and sequencing.

The invention will be further understood with reference to the following experimental examples:

EXAMPLES

The following are examples of general techniques which may be applied in carrying out the method of the invention.

Clusters can be made as described in published reference WO07010251, the protocols of which are incorporated herein by reference.

Example 1

Acrylamide Coating of Glass Chips

The solid supports used are typically 8-channel glass chips such as those provided by Silex Microsystems (Silex Microsystems, Sweden), Micronit (Twente, Nederland) or IMT (Neuchâtel, Switzerland). However, the experimental conditions and procedures are readily applicable to other solid supports.

Chips were washed as follows: neat Decon for 30 min, milliQ H$_2$O for 30 min, NaOH 1N for 15 min, milliQ H$_2$O for 30 min, HCl 0.1N for 15 min, milliQ H$_2$O for 30 min.

Polymer Solution Preparation

For 10 ml of 2% polymerisation mix.

10 ml of 2% solution of acrylamide in milliQ H2O

165 µl of a 100 mg/ml N-(5-bromoacetamidylpentyl) acrylamide (BRAPA) solution in DMF (23.5 mg in 235 µl DMF)

11.5 µl of TEMED

100 µl of a 50 mg/ml solution of potassium persulfate in milliQ H$_2$O (20 mg in 400 µl H$_2$O)

The 10 ml solution of acrylamide was first degassed with argon for 15 min. The solutions of BRAPA, TEMED and potassium persulfate were successively added to the acrylamide solution. The mixture was then quickly vortexed and used immediately. Polymerization was then carried out for 1 h 30 at RT. Afterwards the channels were washed with milliQ H$_2$O for 30 min. The slide was then dried by flushing argon through the inlets and stored under low pressure in a desiccator.

Example 2

Synthesis of N-(5-bromoacetamidylpentyl) acrylamide (BRAPA)

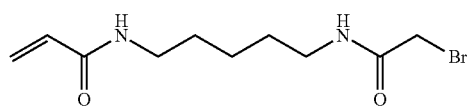

(1)

N-Boc-1,5-diaminopentane toluene sulfonic acid was obtained from Novabiochem. The bromoacetyl chloride and acryloyl chloride were obtained from Fluka. All other reagents were Aldrich products.

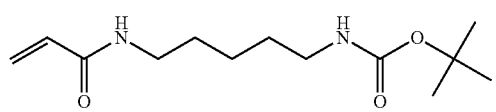

(2)

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether:ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. $^1$H NMR (400 MHz, d$_6$-DMSO): 1.20-1.22 (m, 2H, CH$_2$), 1.29-1.43 (m, 13H, tBu, 2×CH$_2$), 2.86 (q, 2H, J=6.8 Hz and 12.9 Hz, CH$_2$), 3.07 (q, 2H, J=6.8 Hz and 12.9 Hz, CH$_2$), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for C$_{13}$H$_{24}$N$_2$O$_3$ 256, found 279 (256+Na$^+$).

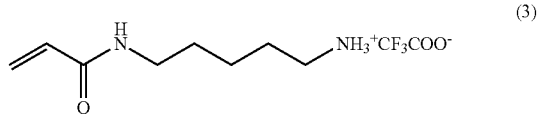

(3)

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). $^1$H NMR (400 MHz, D$_2$O): 1.29-1.40 (m, 2H, CH$_2$), 1.52 (quint., 2H, J=7.1 Hz, CH$_2$). 1.61 (quint., 2H, J=7.7 Hz, CH$_2$), 2.92 (t, 2H, J=7.6 Hz, CH$_2$), 3.21 (t, 2H, J=6.8 Hz, CH$_2$), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for C$_8$H$_{16}$N$_2$O 156, found 179 (156+Na$^+$).

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a dewar). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. $^1$H NMR (400 MHz, d$_6$-DMSO): 1.21-1.30 (m, 2H, CH$_2$), 1.34-1.48 (m, 4H, 2×CH$_2$), 3.02-3.12 (m, 4H, 2×CH$_2$), 3.81 (s, 2H, CH$_2$), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for C$_{10}$H$_{17}$BrN$_2$O$_2$ 276 or 278, found 279 (278+H$^+$), 299 (276+Na$^+$).

Example 3

Grafting of Primers

An SFA coated flowcell is placed onto a modified MJ-Research thermocycler and attached to a peristaltic pump. Grafting mix consisting of 0.5 µM of a forward primer and 0.5 µM of a reverse primer in 10 mM phosphate buffer (pH 7.0) is pumped into the channels of the flowcell at a flow rate of 60 µl/min for 75 s at 20° C. The thermocycler is then heated to 51.6° C., and the flowcell is incubated at this temperature for 1 hour. During this time, the grafting mix undergoes 18 cycles of pumping: grafting mix is pumped in at 15 µl/min for 20 s, then the solution is pumped back and forth (5 s forward at 15 µl/min, then 5 s backward at 15 µl/min) for 180 s. After 18 cycles of pumping, the flowcell is washed by pumping in 5×SSC/5 mM EDTA at 15 µl/min for 300 s at 51.6° C. The thermocycler is then cooled to 20° C.

The primers are typically 5'-phosphorothioate oligonucleotides incorporating any specific sequences or modifications required for cleavage. Their sequences and suppliers vary according to the experiment for which they are used, and in this case are complementary to the 5'-ends of the template duplex. For the experiment described, the amplified clusters contained a diol linkage in one of the grafted primers. Diol linkages can be introduced by including a suitable phosphoramidite intermediate into one of the primers used for solid-phase amplification, for example, as described in WO07010251.

The grafted primers contain a sequence of T bases at the 5'-end to act as a spacer group to aid linearisation and hybridization. Oligonucleotides were prepared using the diol phosphoramidite using standard coupling conditions on a commercial DNA synthesiser. The final cleavage/deprotection step in ammonia cleaves the acetate groups from the protected diol moiety, so that the oligonucleotide in solution contains the diol modification. The sequences of the two primers grafted to the flowcell are:

P5 = 5'-PS-TTTTTTTTT-Diol-AATGATACGGCGACCACCGA-3'
And

P7 = 5'-PS-TTTTTTTTTCAAGCAGAAGACGGCATACGA-3'

Example 4

Cluster Formation

Figure 2:
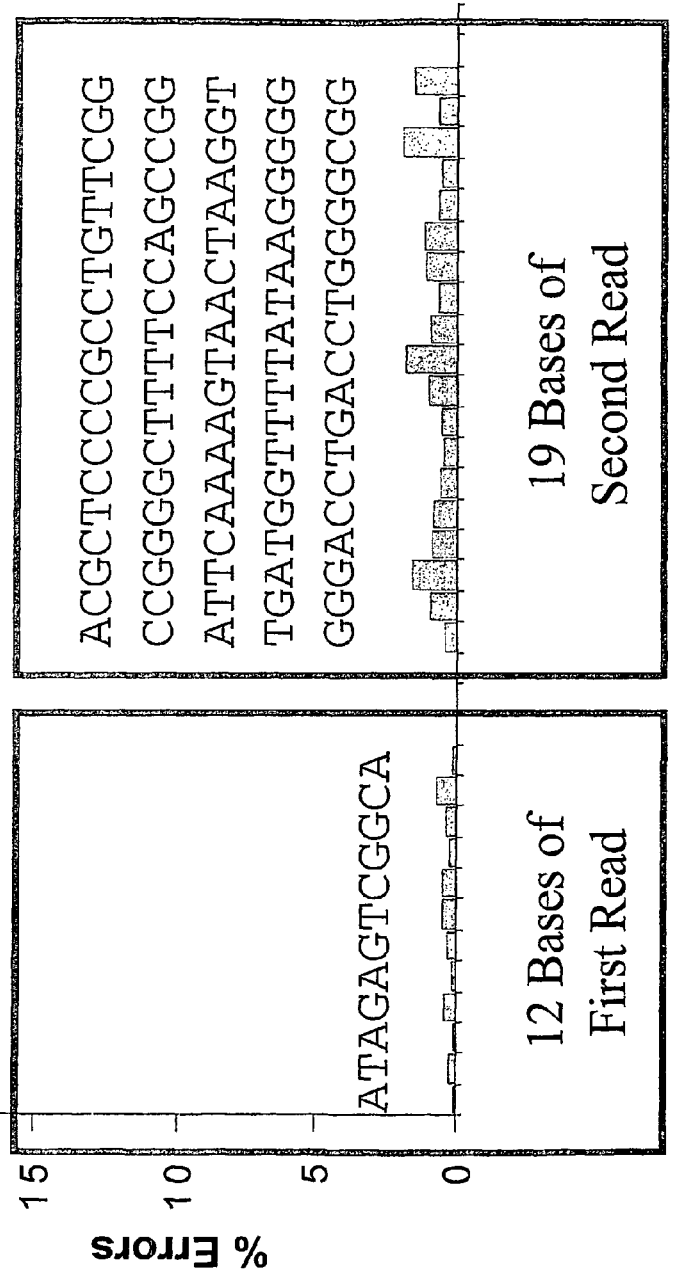
FIG. 2 shows results from sequencing reactions on a mixture of five different template sequences amplified to form clusters.

The DNA sequence used in the amplification process is a mixture of five single monotemplate sequences, with ends complementary to the grafted primers. The full sequence of one of the monotemplate duplexes is shown in FIG. 12, and the sequences or the 19 base variable target region is shown in FIG. 2. The duplex DNA (1 nM) is denatured using 0.1 M sodium hydroxide treatment followed by snap dilution to the desired 0.2-2 pM 'working concentration' in 'hybridization buffer' (5×SSC/0.1% Tween).

Surface amplification was carried out by thermocycling using an MJ Research thermocycler, coupled with an 8-way peristaltic pump Ismatec IPC ISM931 equipped with Ismatec tubing (orange/yellow, 0.51 mm ID).

The single stranded template is hybridised to the grafted primers immediately prior to the amplification reaction, which thus begins with an initial primer extension step rather than template denaturation. The hybridization procedure begins with a heating step in a stringent buffer to ensure complete denaturation prior to hybridisation. After the hybridization, which occurs during a 20 min slow cooling step, the flowcell was washed for 5 minutes with a wash buffer (0.3×SSC/0.1% Tween).

A typical amplification process is detailed in the following table, detailing the flow volumes per channel:

| Step | Description | T (° C.) | Time (sec) | Flow rate (µl/min) | Pumped V (µl) |
|---|---|---|---|---|---|
| 1 | Pump Hybridization pre-mix | 20 | 120 | 60 | 120 |
| 2 | Pump Hybridization mix | 98.5 | 300 | 15 | 75 |
| 3 | Remove bubbles | 98.5 | 10 | 100 | 16.7 |
| 4 | Stop flow and hold T | 98.5 | 30 | static | 0 |
| 5 | Slow cooling | 98.5–40.2 | 19.5 min | static | 0 |
| 6 | Pump wash buffer | 40.2 | 300 | 15 | 75 |
| 7 | Pump amplification pre-mix | 40.2 | 200 | 15 | 50 |
| 8 | Pump amplification mix | 40.2 | 75 | 60 | 75 |
| 9 | First Extension | 74 | 90 | static | 0 |
| 10 | Denaturation | 98.5 | 45 | static | 0 |
| amp cycles 1 to 30 | Re-fill channels | 98.5 | 10 | 60 | 10 |
| | Annealing | 58 | 90 | static | 0 |
| | Extension | 74 | 90 | static | 0 |
| 11 | Hold at 20° C. | 20 | for ever | static | 0 |
| 12 | Pump wash buffer | 74 | 300 | 15 | 75 |

Hybridisation pre mix (buffer) = 5 × SSC/0.1% Tween
Hybridisation mix = 0.1 M hydroxide DNA sample, diluted in hybridisation pre mix
Wash buffer = 0.3 × SSC/0.1% Tween
Amplification pre mix = 2 M betaine, 20 mM Tris, 10 mM
Ammonium Sulfate, 2 mM Magnesium sulfate, 0.1% Triton, 1.3% DMSO, pH 8.8
Amplification mix = 2 M betaine, 20 mM Tris, 10 mM Ammonium
Sulfate, 2 mM Magnesium sulfate, 0.1% Triton, 1.3% DMSO, pH 8.8 plus 200 µM dNTP mix and 25 units/mL of Taq polymerase (NEB Product ref M0273L)

The clusters can be treated in a number of ways to allow sequencing:

Example 5

Sequencing of Non-linearised Clusters

All channels were then denatured by pumping through 0.1M NaOH for 5 minutes at 15 microliters/minute. To aid strand separation, the chip containing NaOH was heated to 80 degrees C., and sequencing primer in hybridisation buffer (0.3×SSC) was flushed in for 5 minutes at 15 microliters/minute. The chip was then cooled to 66 degrees C. and incubated at this temperature for 15 minutes.

The chip was cooled to 40 degrees C., and washed for 5 minutes in 0.1×SSC/0.1% Tween.

Cycles of sequencing enzymology were performed as described below, showing incorporation on non-linearised clusters as well as linearised clusters. Analysis of these images has revealed the extent of incorporation on the non-linearised clusters to be about half that of linearised clusters.

Following denaturation with 0.1 M NaOH, a second sequencing primer was hybridised to give a second sequencing run from the other strand of the template.

Example 6

Sequencing of Linearised Clusters Using Two Hybridisation Steps onto a Single Stranded Template Step 1: Linearisation
To linearize the nucleic acid clusters formed within the flow cell channels, the linearization buffer is flowed through the flow cell for 20 mins at room temp at 15 µL/min (total volume=300 µL per channel), followed by water for 5 mins at r.t.

The linearisation buffer consists of 1429 μL of water, 64 mg of sodium periodate, 1500 μL of formamide, 60 μL of 1 M Tris pH 8, and 11.4 μL of 3-aminopropanol, mixed for a final volume of 3 mL. The periodate is first mixed with the water while the Tris is mixed with the formamide. The two solutions are then mixed together and the 3-aminopropanol is added to that mixture.

Step 2: Blocking Extendable 3'-OH Groups

To prepare the blocking pre-mix, 1360 μL of water, 170 μL of 10× blocking buffer (NEB buffer 4; product number B7004S), and, 170 μL of cobalt chloride (25 mM) are mixed for a final volume of 1700 μL. To prepare the blocking mix, 1065.13 μL of blocking pre-mix, 21.12 μL of 125 μM ddNTP mix, and 13.75 μL of TdT terminal transferase (NEB; part no M0252S) are mixed to a final volume of 1100 μL.

To block the nucleic acid within the clusters formed in the flow cell channels, the blocking buffer is flowed through the flow cell, and the temperature is adjusted as shown in the exemplary embodiments below.

| Step | Description | T (° C.) | Time (sec) | Flow rate (μl/min) | Pumped V (μl) |
|---|---|---|---|---|---|
| 1 | Pump Blocking pre-mix | 20 | 200 | 15 | 50 |
| 2 | Pump Blocking mix | 37.7 | 300 | 15 | 75 |
| 3 | Stop flow and hold T | 37.7 | 20 | static | 0 |
| 4 | Cyclic pump Blocking mix and wait | 37.7 | 8 × (20 + 180) | 15/ static | 45 |
| 5 | Pump wash buffer | 20 | 300 | 15 | 75 |

Step 3: Denaturation and Hybridization of Sequencing Primer

To prepare the primer mix, 895.5 μL of hybridization pre-mix/buffer and 4.5 μl of sequencing primer (100 μM) are mixed to a final volume of 900 μL. The sequences of the two sequencing primers used in these reactions are as follows:

```
Seq primer for first read:
5' AATGATACGGCGACCACCGAGATGAAGGTATAGAT

Seq primer for second read:
5' ACACTCTTTCCCTACACGACGCTCTTCCGATC
```

To denature the nucleic acid within the clusters and to hybridize the sequencing primer, the appropriate solutions are flowed through the flow cell as described below:

| Step | Description | T (° C.) | Time (sec) | Flow rate (μl/min) | Pumped V (μl) |
|---|---|---|---|---|---|
| 1 | Pump 0.1 M NaOH | 20 | 300 | 15 | 75 |
| 2 | Pump TE | 20 | 300 | 15 | 75 |
| 3 | Pump Primer mix | 20 | 300 | 15 | 75 |
| 4 | Hold at 60C | 60 | 900 | 0 | 0 |
| 5 | Pump wash buffer | 40.2 | 300 | 15 | 75 |

After the first sequencing run, this process can be repeated to remove the first run and hybridise the second sequencing primer. After denaturation and hybridization of the sequencing primer, the flowcell is ready for sequencing.

Example 7

DNA Sequencing Cycles

Sequencing was carried out using modified nucleotides prepared as described in International patent application WO 2004/018493; and labelled with four different commercially available fluorophores (Molecular Probes Inc.).

A mutant 9° N polymerase enzyme (an exo-variant including the triple mutation L408Y/Y409A/P410V and C223S) was used for the nucleotide incorporation steps.

Incorporation mix, Incorporation buffer (50 mM Tris-HCl pH 8.0, 6 mM MgSO4, 1 mM EDTA, 0.05% (v/v) Tween –20, 50 mM NaCl) plus 110 nM YAV exo-C223S, and 1 μM each of the four labelled modified nucleotides, was applied to the clustered templates, and heated to 45° C.

Templates were maintained at 45° C. for 30 min, cooled to 20° C. and washed with Incorporation buffer, then with 5×SSC/0.05% Tween 20. Templates were then exposed to Imaging buffer (100 mM Tris pH 7.0, 30 mM NaCl, 0.05% Tween 20, 50 mM sodium ascorbate, freshly dissolved).

Templates were scanned in 4 colours at room temp.

Templates were then exposed to sequencing cycles of Cleavage and Incorporation as follows:

Cleavage
    Prime with Cleavage buffer (0.1 M Tris pH 7.4, 0.1 M NaCl and 0.05% Tween 20). Heat to 60° C.
    Treat the clusters with Cleavage mix (100 mM TCEP in Cleavage buffer).
    Wait for a total of 15 min in addition to pumping fresh buffer every 4 min.
    Cool to 20° C.
    Wash with Enzymology buffer.
    Wash with 5×SSC/0.05% Tween 20.
    Prime with Imaging buffer.
    Scan in 4 colours at RT.
Incorporation
    Prime with Incorporation buffer Heat to 60° C.
    Treat with Incorporation mix. Wait for a total of 15 min in addition to pumping fresh Incorporation mix every 4 min.
    Cool to 20° C.
    Wash with Incorporation buffer.
    Wash with 5×SSC/0.05% Tween 20.
    Prime with imaging buffer.
    Scan in 4 colours at RT.
    Repeat the process of Incorporation and Cleavage for as many cycles as required.

Incorporated nucleotides were detected using a total internal reflection based fluorescent CCD imaging apparatus.

Figure 3:
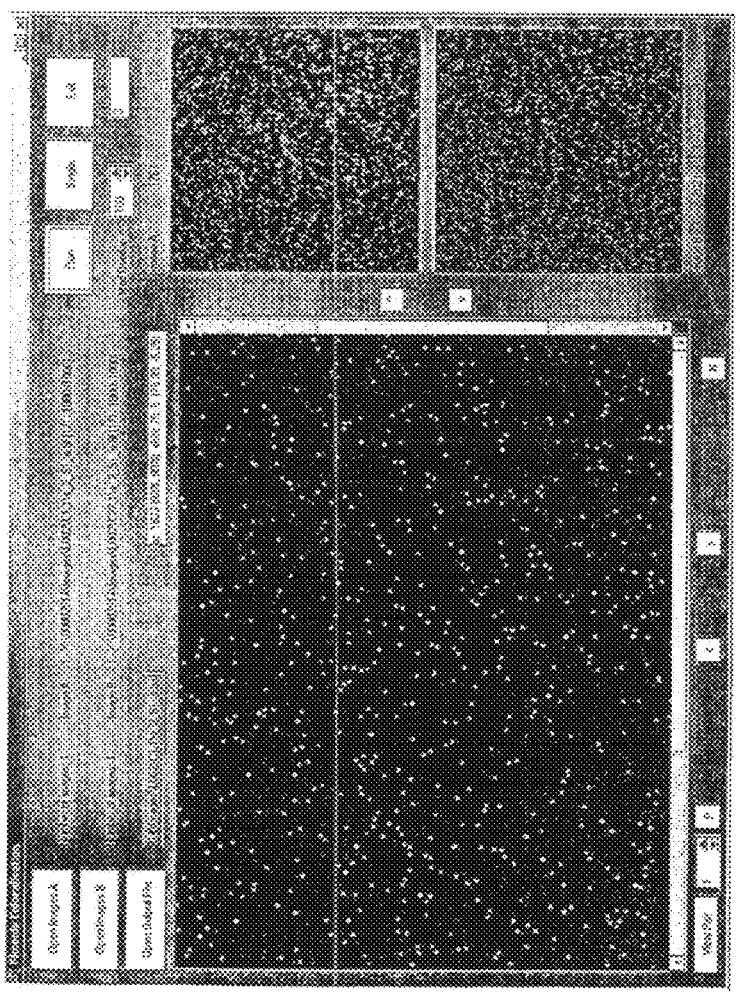
FIG. 3 shows results from sequencing reactions. The images shown are generated from A incorporations. 92% of the run 1 clusters align with run 2. >99% are detected in run 2.

A schematic representation of the method of the present invention is shown in FIG. 1. Data from sequencing reactions is shown in FIGS. 2 and 3. The sequencing data from each run was of comparable quality, and >99% of the clusters from the first run also generated sequencing data from the second run. Moreover, each of the sequences from the second run could be aligned against one of the five expected sequences from the library. This data clearly shows that it is possible to hybridise a first sequencing primer to a linearised cluster, obtain a sequencing read, remove the first extended primer, hybridise a second primer and obtain a second read. Although the data shown was obtained on a mixture of single templates of known sequence to verify that the method was effective, the sequence of the template is not material to the effectiveness of the invention, and therefore any template or 3'- and 5' modified library of templates prepared and amplified using the methods described herein falls within the scope of the invention.

The invention claimed is:

1. A method for pairwise sequencing of first and second regions of a double stranded polynucleotide wherein said first and second regions are in the same target double stranded polynucleotide, the method comprising hybridising and reading from a first primer, removing the first primer followed by hybridising and reading from a second primer at a different location in the same target double stranded polynucleotide.

2. The method according to claim 1, wherein the method comprises:
  (a) providing solid support having immobilised thereon a plurality of double stranded template polynucleotides each formed from complementary first and second template strands linked to the solid support at their 5' ends, wherein each double stranded template polynucleotide comprises a target double stranded polynucleotide;
  (b) treating the plurality of double stranded template polynucleotides to denature said double stranded template polynucleotides to allow hybridisation of a sequencing primer;
  (c) hybridising a first sequencing primer to one of the template polynucleotides generated in part (b);
  (d) carrying out a first sequencing reaction to monitor the incorporation of labeled nucleotides one the first sequencing primer using cycles of primer extension with a polymerase and labeled nucleotides to generate a first extended sequencing primer and determine the sequence of a first region of the template polynucleotide;
  (e) removing the extended sequencing primer from step (d);
  (f) hybridising a second sequencing primer to the one template polynucleotide of step (c) or a complement thereof; and
  (g) carrying out a second sequencing run to monitor the incorporation of labeled nucleotides onto the second sequencing primer using cycles of primer extension with a polymerase and labeled nucleotides to generate a second extended sequencing primer and determine the sequence of a second region of the template polynucleotide, wherein determining the sequences of the first and second regions of the template polynucleotide achieves pairwise sequencing of said first and second regions of said target double-stranded polynucleotide.

3. The method according to claim 1, wherein both strands are attached to a surface, and the first primer is hybridised by heating and cooling.

4. The method according to claim 1, wherein both strands are attached to a surface, and the second primer is hybridised by heating and cooling.

5. The method according to claim 1, wherein both strands are attached to a surface, and the first primer is hybridised after a step of chemical denaturing.

6. The method according to claim 1, wherein both strands are attached to a surface, and the second primer is hybridised after a step of chemical denaturing.

7. The method according to claim 5 or 6, wherein said chemical denaturing is performed using sodium hydroxide solution, formamide solution or urea solution.

8. The method according to claim 7, wherein the concentration of sodium hydroxide solution is greater than 0.05 M.

9. The method according to claim 1, wherein the target double stranded polynucleotide is attached to a surface and comprises an internal known primer region between said first and second regions of the target double stranded polynucleotide and the target double-stranded polynucleotide is denatured to allow hybridisation of a first primer.

10. The method according to claim 9, wherein the internal known primer region comprises a site recognised by a restriction enzyme, and the denaturation process comprises a step of treatment using a restriction enzyme which recognizes said site.

11. The method according to claim 9, wherein the internal known primer region comprises a site recognised by a restriction enzyme, and the denaturation process comprises the steps of using a restriction enzyme which recognizes said site and chemical denaturation to remove non-covalently attached single stranded polynucleotide regions from the surface.

12. The method according to claim 11, wherein said chemical denaturing is performed using sodium hydroxide solution, formamide solution or urea solution.

13. The method according to claim 12, wherein the concentration of sodium hydroxide solution is greater than 0.05 M.

14. The method according to claim 10, wherein said first and second regions of immobilised polynucleotides are sequenced using said first and second primers, said primers being complementary to different regions of the known internal primer at either side of said restriction site.

15. The method according to claim 9, wherein one strand of said double stranded polynucleotide is cleaved from the surface to leave a double stranded polynucleotide immobilised at one end, said double stranded polynucleotide containing two known regions capable of hybridising to a sequencing primer, and said method further comprises denaturing said double stranded polynucleotide to produce an immobilized single stranded polynucleotide.

16. The method according to claim 15, wherein said cleavage step is a chemical or photochemical treatment to cleave the 5'-end of one of the strands of the double stranded polynucleotide.

17. The method according to claim 16, wherein the double stranded polynucleotide is attached via a diol linkage which is cleaved by treatment with a chemical agent comprising periodate.

18. The method according to claim 15, wherein said cleaving involves an enzymatic treatment that cleaves one of the immobilised strands of the polynucleotide.

19. The method according to claim 18, wherein cleavage is performed using a restriction endonuclease.

20. The method according to claim 15, wherein said double stranded polynucleotides are denatured by heating.

21. The method according to claim 15, wherein said double stranded polynucleotides are denatured by chemical denaturation.

22. The method according to claim 21, wherein said chemical denaturation is performed using sodium hydroxide solution, formamide solution or urea solution.

23. The method according to claim 22, wherein the concentration of sodium hydroxide solution is greater than 0.05 M.

24. The method according to claim 1, wherein a plurality of template double stranded polynucleotides are present on a clustered array.

25. The method according to claim 24, wherein the plurality of template double stranded polynucleotides are present within a single cluster on said clustered array.

26. The method according to claim 24, wherein the clustered array is formed by solid-phase nucleic acid amplification.

\* \* \* \* \*

UNITED STATES PATENT AND TRADEMARK OFFICE
CERTIFICATE OF CORRECTION

| | | |
|---|---|---|
| PATENT NO. | : 8,192,930 B2 | Page 1 of 1 |
| APPLICATION NO. | : 12/223759 | |
| DATED | : June 5, 2012 | |
| INVENTOR(S) | : E. Vermaas et al. | |

It is certified that error appears in the above-identified patent and that said Letters Patent is hereby corrected as shown below:

ON THE TITLE PAGE:

Item (75) Inventors, line 3: delete "Waldon (GB);" and insert -- Walden (GB); --, therefor.

IN THE CLAIMS:

In Column 37, line 46, In Claim 2, delete "providing" and insert -- providing a --, therefor.

In Column 37, line 58, In Claim 2, delete "one" and insert -- onto --, therefor.

In Column 40, line 7, In Claim 17, delete "chemical" and insert -- chemical cleavage --, therefor.

Signed and Sealed this
Seventh Day of August, 2012

David J. Kappos
*Director of the United States Patent and Trademark Office*

SEQUENCE LISTING

<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 1
tttttttttt aatgatacgg cgaccaccga                              30

<210> SEQ ID NO 2
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Diol-modified thymine

<400> SEQUENCE: 2
tttttttttt caagcagaag acggcatacg a                            31

<210> SEQ ID NO 3
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 3
aatgatacgg cgaccaccga gatgaaggta tagat                        35

<210> SEQ ID NO 4
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 4
acactctttc cctacacgac gctcttccga tc                           32

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
acgctccccg cctgttcgg                                          19

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
ccggggcttt tccagccgg                                          19

```
<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
attcaaaagt aactaaggt                                                  19

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8
tgatggtttt ataaggggg                                                  19

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
gggacctgac ctggggcgg                                                  19

<210> SEQ ID NO 10
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 10
atagagtcgg ca                                                         12

<210> SEQ ID NO 11
<211> LENGTH: 401
<212> TYPE: DNA
<213> ORGANISM: Artificial Sequence
<220> FEATURE:
<223> OTHER INFORMATION: Synthetic oligonucleotide: Monotemplate duplex

<400> SEQUENCE: 11
ttccttctgc agcaagcaga agacggcata cgagcattcc tgctgaaccg aacaggcggg      60
gagcgtgatc ggaagagcgt cgtgtaggga aagagtgtga gatcttttat catctccata    120
aaacaaaacc cgccgtagcg agttcagata aaataaatcc ccgcgagtgc gaggattgtt    180
atgtaatatt gggtttaatc atctatatgt tttgtacaga gagggcaagt atcgtttcca    240
ccgtactcgt gataataatt ttgcacggta tcagtcattt ctcgcacatt gcagaatggg    300
gatttgtctt cattagactt ataaaccttc atggaatatt tgtatgccga ctctatatct    360
ataccttcat ctcggtggtc gccgtatcat tctgcagacg t                        401

<210> SEQ ID NO 12
<211> LENGTH: 401
<212> TYPE: DNA
<213> ORGANISM: Artificial Sequence
<220> FEATURE:
<223> OTHER INFORMATION: Synthetic oligonucleotide: Monotemplate duplex
```

-continued

```
<400> SEQUENCE: 12
tgcagacgtc ttactatgcc gctggtggct ctacttccat atctatatct cagccgtatg      60
tttataaggt acttccaaat attcagatta cttctgttta ggggtaagac gttacacgct     120
ctttactgac tatggcacgt tttaataata gtgctcatgc cacctttgct atgaacggga     180
gagacatgtt ttgtatatct actaatttgg gttataatgt attgttagga gcgtgagcgc     240
ccctaaataa aatagacttg agcgatgccg cccaaaacaa aatacctcta ctattttcta     300
gagtgtgaga aagggatgtg ctgcgagaag gctagtgcga ggggcggaca agccaagtcg     360
tccttacgag catacggcag aagacgaacg acgtcttcct t                         401

<210> SEQ ID NO 13
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 13
aatgatacgg cgaccaccga gatgaaggta tagat                                 35

<210> SEQ ID NO 14
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 14
acactctttc cctacacgac gctcttccga tc                                    32
```